US009744119B2

(12) United States Patent
Phukan et al.

(10) Patent No.: US 9,744,119 B2
(45) Date of Patent: *Aug. 29, 2017

(54) COSMETIC COMPOSITION AND METHOD OF PREPARATION

(71) Applicant: Momentive Performance Materials Inc., Waterford, NY (US)

(72) Inventors: Monjit Phukan, Bangalore (IN); Anubhav Saxena, Bangalore (IN); Tushar Navale, Mumbai (IN)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/335,917

(22) Filed: Oct. 27, 2016

(65) Prior Publication Data

US 2017/0042787 A1  Feb. 16, 2017

Related U.S. Application Data

(63) Continuation-in-part of application No. 14/572,108, filed on Dec. 16, 2014, now abandoned.

(51) Int. Cl.
| | | |
|---|---|---|
| A61K 9/00 | (2006.01) |
| A61K 8/899 | (2006.01) |
| A61K 8/891 | (2006.01) |
| A61Q 17/04 | (2006.01) |
| A61K 8/35 | (2006.01) |
| A61K 8/49 | (2006.01) |
| A61Q 1/02 | (2006.01) |
| A61K 31/455 | (2006.01) |
| A61K 47/34 | (2017.01) |
| A61K 9/06 | (2006.01) |
| A61K 8/368 | (2006.01) |
| A61K 8/42 | (2006.01) |

(Continued)

(52) U.S. Cl.
CPC .............. *A61K 8/899* (2013.01); *A61K 8/042* (2013.01); *A61K 8/35* (2013.01); *A61K 8/368* (2013.01); *A61K 8/42* (2013.01); *A61K 8/4926* (2013.01); *A61K 8/602* (2013.01); *A61K 8/891* (2013.01); *A61K 9/06* (2013.01); *A61K 31/455* (2013.01); *A61K 47/34* (2013.01); *A61Q 1/02* (2013.01); *A61Q 17/04* (2013.01); *A61K 2800/95* (2013.01)

(58) Field of Classification Search
CPC .................................................... A61K 8/899
See application file for complete search history.

(56) References Cited

U.S. PATENT DOCUMENTS

| | | |
|---|---|---|
| 3,159,601 A | 12/1964 | Ashby |
| 3,159,662 A | 12/1964 | Ashby |

(Continued)

FOREIGN PATENT DOCUMENTS

| | | |
|---|---|---|
| JP | 06-247835 A | 2/1993 |
| JP | 06-247827 A | 9/1994 |
| WO | 00/08087 A1 | 2/2000 |

OTHER PUBLICATIONS

J L. Spier. "Homogeneous Catalysis of Hydrosilation by Transition Metals in Advances In Organometallic Chemistry" vol. 17, (1979) pp. 407-447, F.G.A. Stone & R. West Editors, Academic Press.

(Continued)

*Primary Examiner* — Paul Dickinson
(74) *Attorney, Agent, or Firm* — Joseph S. Ostroff

(57) ABSTRACT

The invention is directed to a cosmetic which comprises an ionic silicone as described herein.

18 Claims, 5 Drawing Sheets

(51) Int. Cl.
*A61K 8/60* (2006.01)
*A61K 8/04* (2006.01)

(56) References Cited

U.S. PATENT DOCUMENTS

| | | | |
|---|---|---|---|
| 3,220,972 A | 11/1965 | Lamoreaux | |
| 3,445,420 A | 5/1969 | Kookootsedes et al. | |
| 3,715,334 A | 2/1973 | Karstedt | |
| 3,775,452 A | 11/1973 | Karstedt | |
| 3,814,730 A | 6/1974 | Karstedt | |
| 4,256,870 A | 3/1981 | Eckberg | |
| 4,279,717 A | 7/1981 | Eckberg et al. | |
| 4,465,818 A | 8/1984 | Shirahata et al. | |
| 4,562,096 A | 12/1985 | Lo et al. | |
| 4,987,169 A | 1/1991 | Kuwata et al. | |
| 5,354,796 A | 10/1994 | Creecy et al. | |
| 5,493,041 A | 2/1996 | Biggs et al. | |
| 5,629,387 A | 5/1997 | Frances et al. | |
| 5,654,362 A | 8/1997 | Schulz, Jr. et al. | |
| 5,663,752 A | 9/1997 | Imamura et al. | |
| 5,760,116 A | 6/1998 | Kilgour et al. | |
| 5,811,487 A | 9/1998 | Schulz, Jr. et al. | |
| 6,124,490 A | 9/2000 | Gormley et al. | |
| 6,296,869 B1 | 10/2001 | Crotty et al. | |
| 6,423,322 B1 | 7/2002 | Fry | |
| 6,531,540 B1 | 3/2003 | O'Brien | |
| 7,381,769 B2 | 6/2008 | O'Brien | |
| 7,687,574 B2 | 3/2010 | Lu et al. | |
| 7,700,530 B2 | 4/2010 | Mundschau et al. | |
| 7,833,541 B2 | 11/2010 | Lu et al. | |
| 8,697,829 B2 | 4/2014 | Saxena et al. | |
| 8,703,881 B2 | 4/2014 | Saxena et al. | |
| 2006/0079633 A1 | 4/2006 | O'Brien et al. | |
| 2012/0016032 A1 | 1/2012 | Moussou et al. | |
| 2013/0171080 A1 | 7/2013 | Sarkar et al. | |
| 2013/0172192 A1 | 7/2013 | Saxena et al. | |
| 2013/0172193 A1 | 7/2013 | Saxena et al. | |
| 2013/0172419 A1 | 7/2013 | Saxena et al. | |
| 2013/0172427 A1 | 7/2013 | Saxena et al. | |
| 2013/0172510 A1 | 7/2013 | Saxena et al. | |
| 2014/0017188 A1 | 1/2014 | Sarkar et al. | |
| 2014/0031734 A1 | 1/2014 | Saxena et al. | |

OTHER PUBLICATIONS

U.S. Appl. No. 14/572,139 for Applicants Alok Sarkar et al., filed Dec. 16, 2014.
U.S. Appl. No. 14/572,132 for Applicants Anubhav Saxena et al., filed Dec. 16, 2014.
U.S. Appl. No. 14/572,118 for Applicants Monjit Phukan et al., filed Dec. 16, 2014.
International Search Report and Written Opinion dated Mar. 15, 2016.

COSMETIC COMPOSITION AND METHOD OF PREPARATION

This application is a continuation in part of U.S. patent application Ser. No. 14/572,108 filed on Dec. 16, 2014 which is incorporated by reference herein.

FIELD OF THE INVENTION

The present invention relates to cosmetic compositions, specifically cosmetic compositions containing crosslinked silicone polymers that have the benefits of compatibility with hydrophilic components and solid particulates.

BACKGROUND OF THE INVENTION

The cosmetic industry thrives on being able to deliver multiple performance products based on mixtures of several components, with each having performance characteristics important to or desirable in the final formulation. One desirable characteristic is the ability to provide a silky initial feel in the cosmetic formulation.

Silicone copolymer gels are known in the cosmetic industry for many uses including their use in skin care applications. However these gels often fail to provide the desired degree of wash-off resistance, pigment dispersibility and anti-whitening properties.

In addition, such silicone copolymer gels have typically been made by methods of generating crosslinked siloxane polymers that limit the range of desirable organofunctional groups that may be incorporated into the polymeric structure to create additional performance advantages in complex cosmetic formulations.

SUMMARY OF THE INVENTION

The invention is directed to a cosmetic which contains an ionically-modified silicone.

In one embodiment herein there is provided a cosmetic composition comprising an oil phase and optionally an aqueous phase wherein the cosmetic composition is made by adding a crosslinked ionic silicone network gel to the oil phase of the cosmetic composition, and wherein the crosslinked ionic silicone network gel is made by combining (a) an ionic silicone network which comprises the reaction product of a crosslinking reaction mixture comprising at least one ionic silicone of the general formula (I):

$$M^1_a M^2_b M^3_c D^1_d D^2_e D^3_f T^1_g T^2_h T^3_i Q_j \qquad (I)$$

wherein:
$M^1 = R^1 R^2 R^3 SiO_{1/2}$
$M^2 = R^4 R^5 R^6 SiO_{1/2}$
$M^3 = R^7 R^8 R^9 SiO_{1/2}$
$D^1 = R^{10} R^{11} SiO_{2/2}$
$D^2 = R^{12} R^{13} SiO_{2/2}$
$D^3 = R^{14} R^{15} SiO_{2/2}$
$T^1 = R^{16} SiO_{3/2}$
$T^2 = R^{17} SiO_{3/2}$
$T^3 = R^{18} SiO_{3/2}$
$Q = SiO_{4/2}$ where $R^1$, $R^2$, $R^3$, $R^4$, $R^5$, $R^6$, $R^8$, $R^9$, $R^{10}$, $R^{11}$, $R^{13}$, $R^{15}$, $R^{16}$ are aliphatic, aromatic or fluoro containing monovalent hydrocarbon radicals containing from 1 to about 60 carbon atoms, specifically from 1 to about 20 carbon atoms and more specifically from 1 to about 8 carbon atoms;

where $R^4$, $R^{12}$, $R^{17}$ are monovalent radical bearing ion-pairs, where $R^7$, $R^{14}$ and $R^{18}$ are independently selected from hydrogen, $-OR^{20}$, unsaturated monovalent radicals or monovalent epoxy group-containing radicals, monovalent sulfur atom-containing radicals and monovalent organosilane groups, wherein $R^{20}$ is selected from hydrogen, monovalent hydrocarbon radical of from 1 to about 60 carbon atoms specifically from 1 to about 20 carbon atoms, more specifically from 1 to about 8 carbon atoms, where the subscript a, b, c, d, e, f, g, h, i, j are zero or positive subject to the following limitations: the sum a+b+c+d+e+f+g+h+i+j is greater than or equal to 2 and less than or equal to 6000, specifically a+b+c+d+e+f+g+h+i+j is greater than or equal to 2 and less than or equal to 4000, more specifically a+b+c+d+e+f+g+h+i+j is less than or equal to 2000, b+e+h is greater than 0;

(b) at least one cosmeceutical active, and
(c) optionally one or more cosmetically acceptable additives; and, shearing the combined components (a), (b) and optionally (c) during and/or after the combining step with a solvent to form the crosslinked ionic silicone network gel.

DETAILED DESCRIPTION OF THE INVENTION

Figure 1:
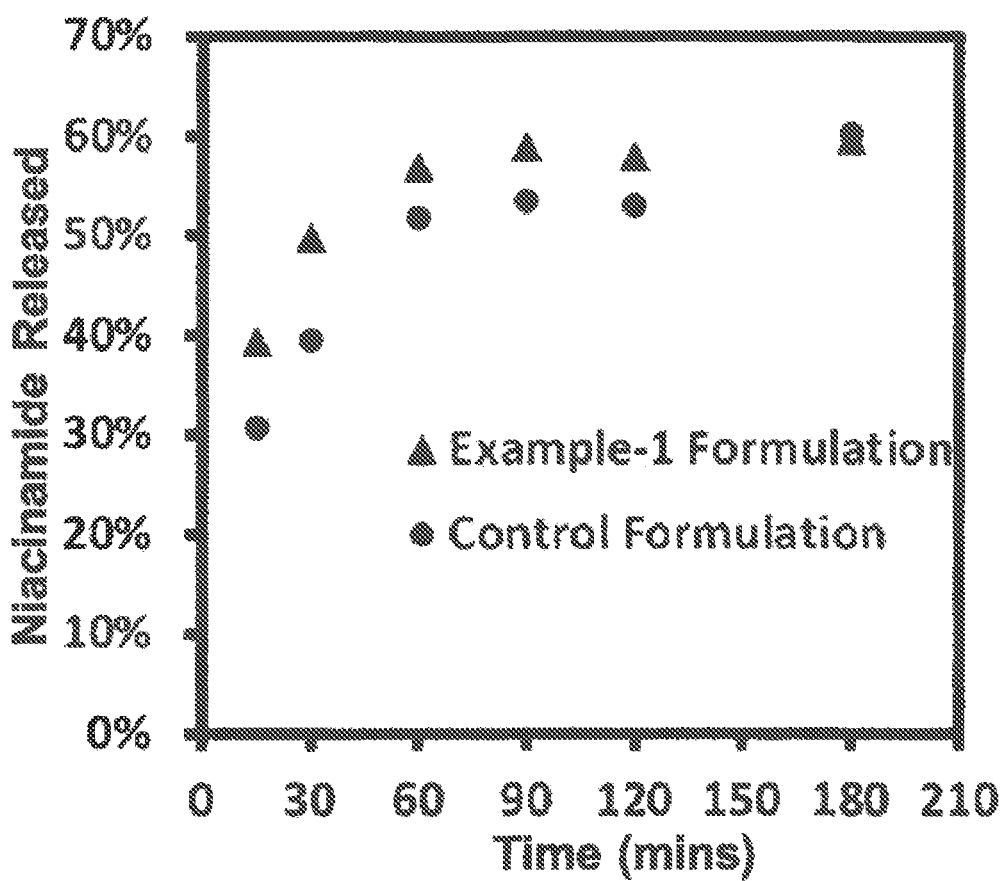
FIG. 1 is a graph illustrating the % release of Niacinamide from the control & example-1 formulation.

The inventors herein have unexpectedly discovered a cosmetic which contains an ionic silicone. The cosmetic can provide for good sensory benefits to the skin, e.g., a silky feel, while also providing the desired degree of cosmetic and/or dermatological benefit, pigment dispersibility and anti-whitening properties.

Other than in the working examples or where otherwise indicated, all numbers expressing amounts of materials, reaction conditions, time durations, quantified properties of materials, and so forth, stated in the specification and claims are to be understood as being modified in all instances by the term "about" whether or not the term "about" is used in the expression.

It will be understood that any numerical range recited herein includes all sub-ranges within that range and any combination of the various endpoints of such ranges or sub-ranges, be it described in the examples or anywhere else in the specification.

It will also be understood herein that any of the components of the invention herein as they are described by any specific genus or species detailed in the examples section of the specification, can be used in one embodiment to define an alternative respective definition of any endpoint of a range elsewhere described in the specification with regard to that component, and can thus, in one non-limiting embodiment, be used to supplant such a range endpoint, elsewhere described.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

Reactants and components referred to by chemical name or formula in the specification or claims hereof, whether referred to in the singular or plural, may be identified as they exist prior to coming into contact with another substance referred to by chemical name or chemical type (e.g., another reactant or a solvent). Preliminary and/or transitional chemical changes, transformations, or reactions, if any, that take place in the resulting mixture, solution, or reaction medium may be identified as intermediate species, master batches, and the like, and may have utility distinct from the utility of the reaction product or final material. Other subsequent changes, transformations, or reactions may result from bringing the specified reactants and/or components together under the conditions called for pursuant to this disclosure. In these other subsequent changes, transformations, or reactions the reactants, ingredients, or the components to be brought together may identify or indicate the reaction product or final material.

In describing the products of the instant invention as a reaction product of initial materials reference is made to the initial species recited and it is to be noted that additional materials may be added to the initial mixture of synthetic precursors. These additional materials may be reactive or non-reactive. The defining characteristic of the instant invention is that the reaction product is obtained from the reaction of at least the components listed as disclosed. Non-reactive components may be added to the reaction mixture as diluents or to impart additional properties unrelated to the properties of the composition prepared as a reaction product. Thus for example particulate solids such as pigments may be dispersed into the reaction mixture, before during or after reaction to produce a reaction product composition that additionally comprises the non-reactive component, e.g. a pigment. Additional reactive components may also be added; such components may react with the initial reactants or they may react with the reaction product; the phrase "reaction product" is intended to include those possibilities as well as including the addition of non-reactive components.

The term "cosmeceutical active" used here and in the claims is defined as cosmetic ingredient that is known in the art to be used for a dermatological treatment such as the non-limiting examples of anti-ageing, anti-wrinkle, anti-acne, anti-dark spot, under eye treatment, anti-blemish, anti-scaring, treatment of sun spots, treatment of stretch marks, treatment of cellulite, and for any other skin appearance treatment.

The term "cosmetically acceptable additives" used here and in the claims is defined as ingredients such as stabilizers, solubilizers, anti-irritants, anti-oxidants and plasticizers, anti-microbials and preservatives which can improve the efficacy and the mechanical properties of the cosmetic formulation.

The term "topical application" used here and in the claims is defined as a formulation which is in contact with the outermost layer of the skin.

It will be understood herein that the expression "oil phase" shall mean that this portion of the cosmetic composition contains one substantially water-insoluble component, optionally a plurality of substantially water-insoluble components. Here, substantially water-insoluble means that the solubility of the components in water alone or as a mixture is less than 10 g/100 g of water, preferably less than 1 g/100 g of water, particularly preferably less than 0.1 g/100 g of water, measured at 20° C., and the pressure of the ambient atmosphere, i.e. from 900 to 1100 hPa. In the case of the oil phase of the cosmetic composition according to the invention, the viscosity of the oil phase, measured at 20° C., and a shear gradient of 10 $sec^{-1}$, is from 0.1 to 1,000,000 mPas, preferably from 0.1 to 500,000 mPas, particularly preferably from 0.2 to 100,000 mPas. In the case of the emulsion according to the invention, the oil phase can preferably contain a plurality of components. The individual components may be both substances which are liquid at 20° C. and solids, the total mixture of the individual components having the above-mentioned viscosity. Preferably, but not necessarily, a multicomponent oil phase is a true solution, i.e. a homogeneous phase in which no further phase interfaces occur.

In addition to water, the "aqueous phase" (which is the other of the two phases present in the personal care composition) may contain further components, such as, preferably, acids, bases, salts, water-soluble organic compounds, such as alcohols, carboxylic acids and derivatives thereof, amines or other organic compounds, polymeric or oligomeric compounds, such as polyols or polyamines or polyamidoamines, complex water-soluble organic compounds, such as cosmetic active substances, dyes, organoelement compounds, such as water-soluble organosilicon compounds or water-soluble transition metal compounds. Optionally, the aqueous phase may contain water-wettable particles, such as pigments, fillers or rheological additives.

The expression "shearing" as used herein is understood to mean either the silicone composition may be further processed to adjust the viscosity and sensory feel of the composition. This may be achieved, for example, by subjecting the composition to a moderate to high shearing force. High shear may be applied using, for example, a Sonolator apparatus, a Gaulin Homogenizer or a Micro Fluidizer apparatus and other methods known in the art. Optionally, one or more fluids may be added to the personal care composition prior to the shearing.

In one embodiment herein, the ionic silicone employed in the cosmetic composition can comprise an ionic silicone composite network made by reacting in a crosslinking reaction mixture at least one ionically modified silicone with the general formula:

$$M^1{}_a M^2{}_b M^3{}_c D^1{}_d D^2{}_e D^3{}_f T^1{}_g T^2{}_h T^3{}_i Q_j \quad (I)$$

wherein:
$M^1 = R^1 R^2 R^3 SiO_{1/2}$
$M^2 = R^4 R^5 R^6 SiO_{1/2}$
$M^3 = R^7 R^8 R^9 SiO_{1/2}$
$D^1 = R^{10} R^{11} SiO_{2/2}$
$D^2 = R^{12} R^{13} SiO_{2/2}$
$D^3 = R^{14} R^{15} SiO_{2/2}$
$T^1 = R^{16} SiO_{3/2}$
$T^2 = R^{17} SiO_{3/2}$
$T^3 = R^{18} SiO_{3/2}$
$Q = SiO_{4/2}$ where $R^1, R^2, R^3, R^4, R^5, R^6, R^8, R^9, R^{10}, R^{11}, R^{13}, R^{15}, R^{16}$ are aliphatic, aromatic or fluoro-containing monovalent hydrocarbon radicals containing from 1 to about 60 carbon atoms, specifically from 1 to about 20 carbon atoms and more specifically from 1 to about 8 carbon atoms, and in some embodiments, the aforestated ranges can have lower limits of 2 or 3 carbon atoms;
where $R^4, R^{12}, R^{17}$ are monovalent or multivalent radical bearing ionic group(s);
where $R^7, R^{14}$ and $R^{18}$ are independently selected from hydrogen, —$OR^{20}$ or unsaturated monovalent hydrocarbon radicals wherein the unsaturated monovalent hydrocarbon radicals contain from 2 to about 60 carbon atoms, more specifically from 2 to about 20 carbon atoms, and most specifically from 2 to about 8 carbon atoms, monovalent oxirane group (e.g., epoxy) containing radicals containing from 2 to about 20 carbon atoms, more specifically from 2 to about 12 carbon atoms and most specifically from 2 to about 8 carbon atoms, monovalent sulfur atom containing radicals of from 1 to about 20 carbon atoms, more specifically from 1 to about 12 carbon atoms and most specifically from 1 to about 12 carbon atoms, monovalent organosilane groups of from 1 to about 20 carbon atoms, more specifically from 1 to about 12 carbon atoms and most specifically from 1 to about 8 carbon atoms wherein each of the organo groups can comprise any one of alkyl, alkenyl, alkoxy and aryl of up to about 12 carbon atoms, and wherein each $R^{20}$ is independently selected from hydrogen and monovalent hydrocarbon radicals of from 1 to about 60 carbon atoms, more specifically from 1 to about 20 carbon atoms, and most specifically from 1 to about 8 carbon atoms, and in some embodiments, the aforestated ranges can have lower limits of any one of 2, 3, 4 or 5 carbon atoms;
where the subscripts a, b, c, d, e, f, g, h, i, j are zero or positive subject to the following limitations: the sum a+b+c+d+e+f+g+h+i+j is greater than or equal to 2 and less than or equal to 6000, specifically a+b+c+d+e+f+g+h+i+j is greater than or equal to 2 and less than or equal to 4000, more specifically a+b+c+d+e+f+g+h+i+j is less than or equal to 2000, and in some embodiments, the aforestated ranges can have lower limits of any one of 3, 4, 5, 10, 12, 18, 20, 30 and 50 as well as 100, 200, 300 and 500, b+e+h is greater than 0, more specifically b+e+h is greater than 1, even more specifically b+e+h is greater than 2, and yet even more specifically b+e+h is from 1 to about 100, further more specifically from 1 to about 50 and most specifically from 1 to about 10, wherein the stated ranges for b+e+h can in some embodiments have lower endpoints of any one of 2, 3, 4, 5, 10, 50 or 100.

In a more specific embodiment, the ionically modified silicone of formula (I), is such that the monovalent ionic radicals $R^4, R^{12}, R^{17}$ are selected from the formula (II):

$$-A-I^{x-}M_n{}^{y+}; \quad (II)$$

where A is a spacing group having selected from a divalent hydrocarbon and hydrocarbonoxy group each containing from 1 to about 60 carbon atoms, more specifically from 1 to about 20 carbon atoms, and most specifically from 1 to about 8 carbon atoms, and in some embodiments, the aforestated ranges can have lower limits of 2 or 3 carbon atoms, wherein the hydrocarbonoxy group contains at least one oxygen heteroatom,
where superscripts x and y are positive integers, such as where x and y are independently from 1 to 6, more specifically from 1 to about 3 subject to the proviso that x is a product of n and y, and each subscript n independently has a value of from 1 to 6, more specifically from about 1 to about 3,
where I is an ionic group such as sulfonate —$SO_3^-$, sulfate —$OSO_3^-$, carboxylate —$COO^-$, phosphonate-$PO_3^{2-}$ and phosphate —$OPO_3^{2-}$ group, more specifically sulfonate —$SO_3^-$, where M is hydrogen or a cation independently selected from alkali metals, alkaline earth metals, rare earth metals, transition metals, metals, metal complexes, quaternary ammonium, polymeric cations and phosphonium groups.

In one specific embodiment herein, A is a divalent arylene group selected from the group consisting of:

—$(CH_2)_l C_6H_4 (CH_2)_k$—,

—$CH_2CH(CH_3)(CH_2)_k C_6H_4$— and,

—$CH_2CH(R^{13*})(CH_2)_l C_6H_3R''$— where $R^{13*}$ is a monovalent hydrocarbon radical having from one to sixty carbon atoms, more specifically, from one to 30 carbon atoms, even more specifically from 1 to 12 carbon atoms and most specifically from 1 to 6 carbon atoms;
where l has a value of 0 to 20, more specifically from 1 to 10 and k has a value of 0 to 20, specifically from 0 to 10.

In another specific embodiment herein, A is a divalent alkylene group of the formula —$(CHR^{14*})_m$— where m has a value of from 1 to 20, specifically from 1 to about 10 and $R^{14*}$ is hydrogen or a monovalent hydrocarbon radical having from one to sixty carbon atoms, more specifically, from one to 30 carbon atoms, even more specifically from 1 to 12 carbon atoms and most specifically from 1 to 6 carbon atoms.

In yet another specific embodiment herein, A is selected from the group consisting of —$CH_2CH_2CH_2$—, —$CH_2CH(CH_3)$—, —$CH_2CH(CH_3)CH_2$—, and $CH_2CH_2CH(CH_2CH_3)CH_2CH_2CH_2$—.

In yet even another specific embodiment herein A is of the formula:

—$(CHR^{20})_m$—O—$(CH(R^{20})(CH_2)$—O$)_{m'}$—X— wherein m has a value of from 2 to 50, more specifically from 2 to about 10 and m' has a value of from 1 to 50, more specifically from 1 to about 25 and $R^{20}$ is hydrogen or a monovalent hydrocarbon radical having from one to sixty carbon atoms, more specifically, from one to 30 carbon atoms, even more specifically from 1 to 12 carbon atoms and most specifically from 1 to 6 carbon atoms and X is null or a divalent hydrocarbon radical optionally containing at least one heteroatom, such as the non-limiting examples of O, N, S or halogen.

In one embodiment herein, M can be a cation independently selected from univalent and polyvalent forms of Li, Na, K, Cs, Mg, Ca, Ba, Zn, Cu, Fe, Ni, Ga, Al, Mn, Cr, Ag, Au, Pt, Pd, Pb, Sb, Ru, Sn and Rh, such as the non-limiting examples of $Mn^{+2}$ and $Mn^{+3}$.

In one non-limiting embodiment herein M can specifically be a cation selected from univalent and polyvalent forms of Na, K, Mg, Ca, Zn, Cu, Fe, Ni, Co and Al.

In another more specific embodiment, the ionically-modified cross-linked silicone network comprising the ionically modified silicone of formula (I), wherein the monovalent radicals $R^4$, $R^{12}$, $R^{17}$ are selected from zwitterions having the formula (III):

$$—R'—NR''_2{}^+—R'''—I \qquad (III)$$

where R' is a divalent hydrocarbon radical containing from 1 to about 60 carbon atoms, specifically from 1 to about 20 carbon atoms, and more specifically from 1 to about 8 carbon atoms and in some embodiments, the aforestated ranges can have lower limits of 2 or 3 carbon atoms, where R" is monovalent hydrocarbon radical containing from 1 to about 60 carbon atoms, specifically from 1 to about 20 carbon atoms and more specifically from 1 to about 8 carbon atoms, and optionally, one or more of a sulfur atom, a nitrogen atom, oxygen atom, and in some embodiments, the aforestated ranges can have lower limits of 2 or 3 carbon atoms, where R'" is divalent hydrocarbon radical containing from 2 to about 20 carbon atoms, specifically from 2 to about 8 carbon atoms and more specifically from 2 to about 4 carbon atoms; and, I is an ionic group such as sulfonate —$SO_3^-$, sulfate —$OSO_3^-$, carboxylate —$COO^-$, phosphonate —$PO_3^{2-}$ group and phosphate —$OPO_3^{2-}$ group.

As used herein the terminology "hydrocarbon radical" includes acyclic hydrocarbon radicals, alicyclic hydrocarbon radicals and aromatic hydrocarbon radicals.

As used herein in reference to a hydrocarbon radical, the term "monovalent" means that the radical is capable of forming one covalent bond per radical, the term "divalent" means that the radical is capable of forming two covalent bonds per radical and the term "trivalent" means that the radical is capable of forming three covalent bonds per radical. Generally, a monovalent radical can be represented as having been derived from a saturated hydrocarbon compound by conceptual removal of one hydrogen atom from the compound, a divalent radical can be represented as having been derived from a saturated hydrocarbon compound by conceptual removal of two hydrogen atoms from the compound and a trivalent radical can be represented as having been derived from a saturated hydrocarbon compound by conceptual removal of three hydrogen atoms from the compound. For example, an ethyl radical, that is, a —$CH_2CH_3$ radical, is a monovalent radical; a dimethylene radical, that is, a —$(CH_2)_2$— radical, is a divalent radical and an ethanetriyl radical, that is,

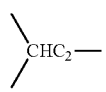

radical, is a trivalent radical, each of which can be represented as having been derived by conceptual removal of one or more hydrogen atoms from the saturated hydrocarbon ethane.

As used herein, the terminology "acyclic hydrocarbon radical" means a straight chain or branched hydrocarbon radical, preferably containing from 1 to 60 carbon atoms per radical, which may be saturated or unsaturated and which may be optionally substituted or interrupted with one or more atoms or functional groups, such as, for example, carboxyl, cyano, hydroxy, halo and oxy. As long as these functional groups do not interfere with the cationic cure mechanism of the epoxide or oxirane moiety, suitable monovalent acyclic hydrocarbon radicals may include, for example, alkyl, alkenyl, alkynyl, hydroxyalkyl, cyanoalkyl, carboxyalkyl, alkyloxy, oxaalkyl, alkylcarbonyloxaalkylene, carboxamide and haloalkyl, such as, for example, methyl, ethyl, sec-butyl, tert-butyl, octyl, decyl, dodecyl, cetyl, stearyl, ethenyl, propenyl, butynyl, hydroxypropyl, cyanoethyl, butoxy, 2,5,8-trioxadecanyl, carboxymethyl, chloromethyl and 3,3,3-fluoropropyl.

Suitable divalent acyclic hydrocarbon radicals include, for example, linear or branched alkylene radicals, such as, for example, methylene, dimethylene, trimethylene, decamethylene, ethylethylene, 2-methyltrimethylene, 2,2-dimethyltrimethylene and linear or branched oxyalkylene radicals such as, for example, methyleneoxypropylene.

Suitable trivalent acyclic hydrocarbon radicals include, for example, alkanetriyl radicals, such as, for example, 1,1,2-ethanetriyl, 1,2,4-butanetriyl, 1,2,8-octanetriyl, 1,2,4-cyclohexanetriyl and oxaalkanetriyl radicals such as, for example, 1,2,6-triyl-4-oxahexane.

As used herein the term "alkyl" means a saturated straight or branched monovalent hydrocarbon radical. In a preferred embodiment, monovalent alkyl groups are selected from linear or branched alkyl groups containing from 1 to 60 carbons per group, such as, for example, methyl, ethyl, propyl, iso-propyl, n-butyl, iso-butyl, sec-butyl, tert-butyl, pentyl, hexyl, heptyl, decyl, dodecyl.

As used herein the term "alkenyl" means a straight or branched monovalent terminally unsaturated hydrocarbon radical, preferably containing from 2 to 10 carbon atoms per radical, such as, for example, ethenyl, 2-propenyl, 3-butenyl, 5-hexenyl, 7-octenyl and ethenylphenyl.

As used herein, the terminology "alicyclic hydrocarbon radical" means a radical containing one or more saturated hydrocarbon rings, specifically containing from 4 to 12 carbon atoms per ring, per radical which may optionally be substituted on one or more of the rings with one or more alkyl radicals, each preferably containing from 2 to 6 carbon atoms per alkyl radical, halo radicals or other functional groups and which, in the case of a monovalent alicyclic hydrocarbon radical containing two or more rings, may be fused rings. Suitable monovalent alicyclic hydrocarbon radicals include, for example, cyclohexyl and cyclooctyl. Suitable divalent hydrocarbon radicals include, saturated or unsaturated divalent monocyclic hydrocarbon radicals, such as, for example, 1,4-cyclohexylene. Suitable trivalent alicyclic hydrocarbon radicals include, for example, cycloalkanetriyl radicals such as, for example, 1-dimethylene-2,4-cyclohexylene, 1-methylethylene-3-methyl-3,4-cyclohexylene.

As used herein, the terminology "aromatic hydrocarbon radical" means a hydrocarbon radical containing one or more aromatic rings per radical, which may, optionally, be substituted on the aromatic rings with one or more alkyl radicals, each preferably containing from 2 to 6 carbon atoms per alkyl radical, halo radicals or other functional groups and which, in the case of a monovalent aromatic hydrocarbon radical containing two or more rings, may be fused rings. Suitable monovalent aromatic hydrocarbon radicals include, for example, phenyl, tolyl, 2,4,6-trimethylphenyl, 1,2-isopropylmethylphenyl, 1-pentalenyl, naphthyl, anthryl, eugenol and allylphenol as well as aralkyl radicals such as, for example, 2-phenylethyl. Suitable divalent aromatic hydrocarbon radicals include, for example, divalent monocyclic arenes such as, for example, 1,2-phenylene, 1,4-phenylene, 4-methyl-1,2-phenylene, phenylmethylene. Suitable trivalent aromatic hydrocarbon radicals include, for example, trivalent monocyclic arenes such as, for example, 1-trimethylene-3,5-phenylene.

In one non-limiting embodiment herein, $R^1$, $R^2$, $R^3$, $R^4$, $R^5$, $R^6$, $R^8$, $R^9$, $R^{10}$, $R^{11}$, $R^{13}$, $R^{15}$ and $R^{16}$ are independently as described herein, and optionally wherein each can contain at least one heteroatom selected from the group consisting of oxygen and halogen.

Some specific non-limiting examples of hydrocarbon radicals that may be used herein, such as in the non-limiting example of the hydrocarbon radicals used for $R^1$, $R^2$, $R^3$, $R^4$, $R^5$, $R^6$, $R^8$, $R^9$, $R^{10}$, $R^{11}$, $R^{13}$, $R^{15}$ and $R^{16}$ that may be suitable are methyl, ethyl, n-propyl, iso-propyl, n-butyl, isobutyl, tert-butyl, n-pentyl, iso-pentyl, neopentyl and tert-pentyl; hexyl, such as the n-hexyl group; heptyl, such as the n-heptyl group; octyl, such as the n-octyl and isooctyl groups and the 2,2,4-trimethylpentyl group; nonyl, such as the n-nonyl group; decyl, such as the n-decyl group; cycloalkyl radicals, such as cyclopentyl, cyclohexyl, cycloheptyl radicals and methylcyclohexyl radicals. Some specific non-limiting examples of aryl hydrocarbon radicals that may be suitable are phenyl, napthyl; o-, m- and p-tolyl, xylyl, ethylphenyl and benzyl.

In one non-limiting embodiment herein, the cosmetic described herein can further comprise one or more of a solvent, a cosmeceutical active, a cosmetically acceptable additive and an excipient.

In one non-limiting embodiment herein, the solvent can be the ionic silicone described herein.

In one non-limiting embodiment herein the solvent is an ionically-modified silicone polymer having the general structure (VI):

 (VI)

wherein:
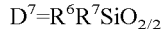
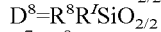
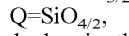

and wherein, the radicals $R^1$, $R^2$, $R^3$, $R^4$, $R^5$, $R^6$, $R^7$, $R^8$ and $R^9$ are independently selected from aliphatic or aromatic monovalent hydrocarbon radicals having from 1 to 60 carbon atoms, more specifically from 1 to 30 carbon atoms, even more specifically from 1 to 12 carbon atoms and most specifically from 1 to 8 carbon atoms, and optionally each containing at least one hetero atom, such as O, N, S and halogen, and in some embodiments, the aforestated ranges can have lower limits of 2 or 3 carbon atoms, and the subscripts $\alpha$, $\beta$, $\chi$, $\delta$, $\epsilon$, $\phi$, and $\gamma$ are zero or positive subject to the following limitations: $2 \leq \alpha+\beta+\chi+\delta+\epsilon+\phi+\gamma \leq 6000$, more specifically $2 \leq \alpha+\beta+\chi+\delta+\epsilon+\phi+\gamma \leq 4000$, and most specifically $2 \leq \alpha+\beta+\chi+\delta+\epsilon+\phi+\gamma \leq 2000$ and the aforestated ranges can have lower limits of any one of 3, 4, 5, 10, 12, 18, 20, 30 and 50 as well as 100, 200, 300 and 500; and, $\beta+\delta+\phi > 0$, more specifically, $\beta+\delta+\phi$ is from 1 to about 100 and more specifically, $\beta+\delta+\phi$ is from 1 to about 50 and most specifically $\beta+\delta+\phi$ is from 1 to about 25, wherein said ranges of $\beta+\delta+\phi$ can have in some embodiments, upper limits of any one of 2, 3, 4, 5, 10, 50 or 100.

In another embodiment herein, solvents which are suitable for use are those compounds or mixtures of two or more compounds that are in a liquid state at or near room temperature, e.g., 20° C. to about 50° C. and about one atmosphere pressure, and include such non-limiting examples as those selected from silicone fluids, hydrocarbon fluids, esters, alcohols, fatty alcohols, glycols, organic waxes and organic oils.

In one embodiment herein the solvent can comprise a blend of two or more solvents.

In yet another embodiment, the silicone fluids may be selected from the group consisting of low viscosity silicone fluids and volatile silicone fluids.

In yet even another embodiment herein, the solvent is at least one selected from the group consisting of isodecane, isohexadecane, hydrogenated polyisobutene, jojoba, cylcopentasiloxane, dimethicone, bis-phenylpropyl dimethicone, octyldodecyl neopentanoate, oleyl oleate, oleyl alcohol and isomyristyl alcohol.

In another embodiment the carrier solvent is a cyclic silicone fluid of the general formula $D_r$, where $D = R^{15}R^{16}SiO_{2/2}$ and where $R^{15}$ and $R^{16}$ are monovalent hydrocarbon radicals of from 1 to 6 carbon atoms, more specifically methyl, and r is an integer of from 3 to 12, more specifically, from 4 to 8. Specifically, the cyclic silicone fluid can be selected from hexamethylcyclotrisiloxane, octamethylcyclotetrasiloxane, decamethylcyclopentasiloxane and dodecamethylcyclohexasiloxane.

In one embodiment, the solvent of the present invention can comprise an emollient compound. Suitable emollient compound include any fluid that provides emollient properties, that is, that when applied to skin, tend to remain on the surface of the skin or in the stratum corneum layer of the skin to act as lubricants, reduce flaking and to improve the appearance of the skin. Emollient compound are generically known and include, for example, hydrocarbons, such as for example, isododecane, isohexadecane and hydrogenated polyisobutene, organic waxes, such as for example, jojoba, silicone fluids, such as, for example, cyclopentasiloxane, dimethicone and bis-phenylpropyl dimethicone, esters, such as, for example, octyldodecyl neopentanoate and oleyl oleate, as well as fatty acids and alcohols, such as for example, oleyl alcohol and isomyristyl alcohol.

In one non-limiting embodiment herein the ionically-modified silicone network is swellable by the solvent.

In another embodiment herein the solvent is a hydrophilic emollient selected from the group consisting of glycerine, sorbitol, aqueous solution of moisturizing additives and combinations thereof.

In one specific embodiment the solvent is selected from a silicone oil, an organic oil and combinations thereof.

Because it is possible to vary the compositional parameters of the ionically-modified silicone network (cross-polymer) composition of the invention in an almost limitless fashion, by varying the compositional parameters of the ionically-modified silicone cross-polymer, some compositions herein are both water swellable and oil swellable while others are only water swellable or oil swellable. The amount of crosslinking present in the ionically-modified silicone cross-polymer may be characterized with respect to the degree of swelling exhibited by the cross-polymer in the solvent. In another embodiment, the crosslinked structure of the ionically-modified silicone cross-polymer is effective to allow the ionically-modified silicone cross-polymer to be swollen from its original volume to a swollen volume that is a factor of from 1.01 to 5000, more preferably from 2 to 1000, and even more preferably from 5 to 500, times its original volume. The original volume of the ionically-modified silicone cross-polymer can be determined, for example, by extracting or evaporating all of the solvent component from the cosmetic composition of the present invention to leave the original volume, that is, the volume of the ionically-modified silicone cross-polymer in the absence of the fluid.

In a more specific embodiment, the cosmetic composition of the present invention comprises, per 100 parts by weight ("pbw") of the ionically-modified silicone cross-polymer, from 1 pbw to 99.9 pbw, more preferably from 70 pbw to 99.5 pbw, and still more preferably from 85 pbw to 99 pbw of the solvent.

Some non-limiting examples of cosmeceutical actives include alpha-hydroxy acids, such as citric acid, glycolic acid, lactic acid, malic acid, pyruvic acid, tartaric acid; antioxidants such as alpha-lipoic acid, L-ascorbic acid (vitamin C), niacinamide (vitamin B3), N-acetyl-glucosamine (NAG), α-tocopherol, and ubiquinone (CoQ10); botanicals such as green tea extract, ferulic acid, and grape-seed extract; depigmenting agents such as hydroquinone, ascorbic acid (vitamin C), kojic acid, and licorice extract (glabridin); exfoliants such as salicylic acid (SA), lactic acid, and glycolic acid; moisturizers; topical peptides; retinoids such as retinoic acid (tretinoin), retinol, and retinaldehyde; and, sunscreens.

The cosmetically acceptable additives and excipients that are suitable for use herein can be any of the skin benefit agents and/or cosmetic ingredients described herein. In addition, the cosmetically acceptable additives and excipients as well as the skin benefits agents or cosmetic ingredients can also comprise ingredients commonly found in photoprotective agents, self-tanning agents, desquamating agents, depigmenting agents, moisturizing agents, skin lightening agents, anti-ageing ingredients, anti-wrinkle agents and combinations thereof.

It will be understood herein that the cosmetic material can comprise any of the cosmetically acceptable additive and excipients, the skin benefit agents and/or cosmetic ingredients or the personal care components or ingredients described herein as well as any other known cosmetic component or cosmetic active ingredient known to those skilled in the art.

In one embodiment herein the combined components (a), (b) and (c) further comprises film-forming additives selected from the group consisting of polysilicone dimethicone, polysilicone acrylate copolymer, dimethylsiloxane/3-thiopropyl methyl siloxane copolymer, vinylpyyrolidone/vinylacetate copolymer, polyvinylacetate, starch, polyquaternium-4, polyquaternium-11, acrylates/steareth-2 methacrylate crosspolymer, vinylacetate/vinyl neodecanoate copolymer, polyester-5, cetyl ethylhexanoate, vinyl acetate, crotonate/vinyl neodecanoate copolymer, 2-acryamido-2-methyl propane sulfonic acid/acrylic acid copolymer, acryamido-2-methyl propane sulfonic acid/acrylic acid/acryl methacrylate copolymer, polyacrylamide, C13-C14 isoparaffin, laureth-7, octylacrylamide, acrylate/butylaminoethylmethacrylate copolymer, and combinations thereof.

In one other embodiment, the combined components (a), (b) and (c) further comprise cross-linked matrixes selected from the group consisting of non-ionic silicone cross-polymers, urethane cross-polymer, acrylated cross-polymers, cross-linked polysaccharides and combinations thereof.

In one other embodiment herein the ionic silicone network (a) can be combined with the cosmetically acceptable additive (c) prior to forming the combination with the cosmeceutical active (b).

In yet one other embodiment the cosmeceutical active (b) is present in the crosslinking reaction mixture with the ionic silicone of formula (I).

In yet a further embodiment, the cosmeceutical active (b) is kept separate from the crosslinking reaction mixture with the ionic silicone of formula (I), and then bother are combined following the formation of the ionic silicone network to form the crosslinked ionic silicone network gel in-situ during a topical application of the cosmetic composition.

It will be understood herein that any of the embodiments described herein can be revised accordingly such that the ionically-modified cross-linked silicone network (i.e., of formula (I)), by combinations of reactants (with the solvent not being a reactant but physically entrained within the reaction product of ionically-modified cross-linked silicone network composition) using any known crosslinking means. In one non-limiting embodiment, the silicone ionomer is of the general formula (I) described herein and is produced by a reaction selected from a condensation reaction, a hydrosilylation reaction, a free-radical polymerization reaction, a ring-opening polymerization reaction and combinations thereof.

In one embodiment, the reaction is conducted as a neat reaction or in the presence of at least one cosmeceutical, cosmetic material or cosmetic active ingredient described herein or known to those skilled in the art.

In another embodiment, the ionic silicone composite network further comprises a physical blend of the silicone ionomer of formula (I) and an organic structuring polymer and/or another network.

In yet another embodiment herein, the hydrosilylation reaction described herein can be used to crosslink the crosslinking reaction mixture which mixture can comprise any of the following:

ionic silyl-hydride silicone with non-ionic olefinic compound (silicone or non-silicone) and non-ionic solvent;
non-ionic silyl-hydride silicone with ionic olefinic compound (silicone or non-silicone) and non-ionic solvent;
ionic silyl-hydride silicone with ionic olefinic compound (silicone or non-silicone) and non-ionic solvent;
non-ionic silyl-hydride silicone with non-ionic olefinic compound (silicone or non-silicone) and ionic solvent;
ionic silyl-hydride silicone with non-ionic olefinic compound (silicone or non-silicone) and ionic solvent;
non-ionic silyl-hydride silicone with ionic olefinic compound (silicone or non-silicone) and ionic solvent;
ionic silyl-hydride silicone with ionic olefinic compound (silicone or non-silicone) and ionic solvent;
ionic functional, silyl-hydride functional and silyl-olefin functional compound with non-ionic solvent; and,
ionic functional, silyl-hydride functional and silyl-olefin functional compound with ionic solvent.

In one non-limiting embodiment herein the crosslinked ionic silicone network can be in the absence of polyether moieties and/or polyether crosslinks. More specifically, the crosslinked ionic silicone network can be in the absence of one or more moieties selected from glycolide, lactide, butyrolactide and caprolactide. In yet a further non-limiting embodiment herein, the crosslinked ionic silicone network can be in the absence of acrylate and/or olefinic functionality. In yet a further non-limiting embodiment, the crosslinked ionic silicone network is in the absence of olefinic and hydride crosslinking.

It will be understood herein that at rest, the crosslinked ionic silicone network gel exhibits the properties of a solid gel material. The gel of the present invention exhibits high stability and resistance to syneresis, that is, the composition exhibits little or no tendency for fluid to flow from the composition and imparts high stability and syneresis resistance to personal care compositions which include the gel as a component in the oil phase. The high stability and syneresis resistance persists with prolonged aging of such cosmetic compositions. However, fluid may be released from the network by subjecting the silicone composition to a shearing force, such as, for example, by rubbing the composition between one's fingers, to provide improved sensory feel characteristic of the fluid component of the cosmetic composition.

In one other embodiment herein there is provided a cosmetic comprising a an oil phase and an aqueous phase which cosmetic is made by the process of adding at least one crosslinked ionic silicone network gel to the oil phase of the personal care composition and wherein the crosslinked ionic silicone network gel is formed by reacting the crosslinking reaction mixture comprising
    i. at least one silicone hydride bearing at least two Si—H residues,
    ii. at least one olefin with two or more Si-unsaturated radicals,
    iii. an effective amount of precious metal catalyst suitable for facilitating addition cure reaction between (a) and b, and
    iv. optionally, a solvent suitable for swelling the said cross-polymer; subject to the limitation that at least one of (i), (ii) or (iv) is selected from an ionically modified silicone of general formula (I):

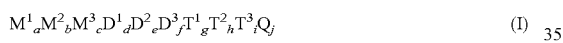
(I)

as described herein; and, shearing the crosslinked ionic silicone network during and/or after the reacting step with at least solvent (as described herein) to form the crosslinked ionic silicone network gel.

In one embodiment herein, the at least one silicone hydride bearing at least two Si—H residues and the silicon hydride activator described below that is used herein is such that it is suitable for either a crosslinking hydrosilylation reaction and/or a ring opening of the oxirane moiety of the oxirane silicone copolymer bearing ionic radicals in order to provide for the crosslinking present in the resultant crosslinked ionic silicone network. It can include any silicon compound derived from at least two organosiloxane units and having terminal and/or pendant Si—H groups. In one embodiment herein the at least one silicone hydride bearing at least two Si—H residues or the silicon-hydride activator is such that it contains at least some Si—H functional units along its polymer backbone. It may or may not in addition to these internal Si—H functional units also contain terminal Si—H functional units.

In one embodiment the at least one silicone hydride bearing at least two Si—H residues or the silicone hydride activator (the Si—H functional silicon compound—as a group comprising both embodiments) in the olefin-hydride reaction is capable of reacting with the olefinic moieties of the above-mentioned oxirane moieties via addition reaction. Examples of suitable Si—H functional silicon compounds include 1,1,3,3-tetraalkyldisiloxane, dialkylhydrogensiloxy-endstopped polydialkylsiloxane, polydialkylalkylhydrogensiloxane copolymer, and trialkylsiloxy-endstopped polydialkyl-alkylhydrogensiloxane copolymer comprising at least two alkylhydrogen siloxy groups. Other examples of Si—H containing silicon compounds include 1,1,3,3-tetramethyldisiloxane, 2,4,6,8-tetramethylcyclotetrasiloxane, methyldimethoxysilane, triethylsilane, and methyldiethoxysilane. The preferred silicon hydride activator used in the present invention is 1,1,3,3-tetramethyldisiloxane.

Although the Si—H functional silicon compound may be a silane, it is most advantageous to use an Si—H functional polysiloxane linear polymer. Thus, one embodiment of the present invention utilizes an Si—H functional linear polysiloxane polymer represented by the formula:

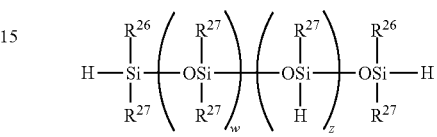

wherein $R^{26}$ and $R^{27}$ are each independently a monovalent hydrocarbon radical of from 1 to about 60 carbon atoms, specifically from 1 to about 20 carbon atoms and more specifically from 1 to about 8 carbon atoms, and in some embodiment, the aforestated ranges can have lower limits of 2 or 3 carbon atoms;

"w" is from 1 to about 1,000; and "z" is from about 5 to about 200. More preferably, "w" varies from about 10 to about 500 and "z" varies from about 5 to about 200.

Another embodiment of the present invention utilizes cyclic silicone hydrides as the Si—H functional silicon compound. Such cyclic silicone hydrides are well known in the art and may be represented by the formula:

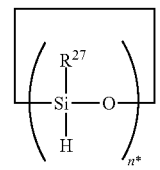

wherein $R^{27}$ is as defined above and "n*" is from about 3 to about 12, specifically from about 4 to about 10.

In one non-limiting embodiment, the amount of the Si—H functional silicon compound present in the cosmetic composition is from about 0.01 pbw to about 10 pbw, more specifically from about 0.05 pbw to about 7 pbw and most specifically from about 0.1 pbw to about 5 pbw based on 100 parts by weight of the olefinic component or the oxirane silicone copolymer bearing ionic radicals.

In one embodiment herein the at least one olefin or silyl-olefin group containing silicone which contains at least two silyl-olefin groups is selected from the group consisting of at least one of non-silicone olefin and organo-modified silicone olefin, wherein the organo-modified silicone olefin has the general structure (V) as described herein.

In another more specific embodiment, the at least one olefin can comprise a combination of a non-silicone olefin such as the non-limiting example of an α,ω-diene, and an organo-modified silicone olefin of the general structure (V) as described herein:

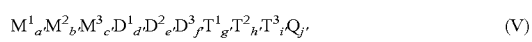
(V)

In one embodiment herein, some non-limiting examples of α,ω-diene include butadiene, hexadiene, octadiene, norbornene, ethylidene norbornene, vinylnorbornene, norbornadiene, and dicyclopentadiene and combinations thereof.

In yet another more specific embodiment, the at least one olefin comprises a blend of at least one multifunctional olefin and a mono-functional olefin.

In another more specific embodiment herein $R^O$ is a monovalent olefin radical having the structure (VII):

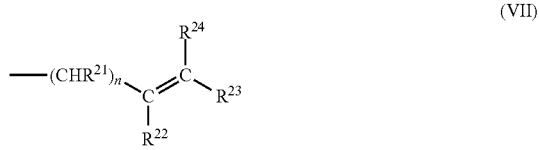

where $R^{21}$, $R^{22}$, $R^{23}$ and $R^{24}$ are each independently selected from the group of hydrogen and monovalent hydrocarbon radicals containing from 1 to 60 carbon atoms, more specifically 1 to 30 carbon atoms, even more specifically from 1 to 12 carbon atoms and most specifically from 1 to about 6 carbon atoms.

In one embodiment, the amounts of hydride-functional silicone (i) and olefin (ii) that is employed in the process(es) described herein can be present in any amount that provides for a molar equivalent amount of silicon-hydride moieties to the molar amount of unsaturated moieties present in the olefin (ii). In one non-limiting embodiment, either the molar amount of silicon-hydride moieties present in the hydride-functional silicone (i) exceed the molar amount of unsaturated moieties present in the olefin (ii) or vice-versa, the molar amount of unsaturated moieties present in the olefin (ii) exceed the molar amount of silicon-hydride moieties present in the hydride-functional silicone (i). In a more specific embodiment the amount of hydride-functional silicone (i) that is employed in the process(es) described herein can be present in any equivalent amount that provides for a molar ratio of silicon-hydride moieties in silicone (i) to unsaturated moieties in olefin (ii) of from 1:100 to about 100:1, more specifically from about 1:10 to about 10:1.

In one embodiment herein the solvent (iv) can be any of the solvent described herein.

In one embodiment herein, the amount of solvent (iv) that can be employed in the process(es) and compositions described herein comprise from about 0 weight percent to about 99.9 weight percent, more specifically from about 0 weight percent to about 99 weight percent and most specifically from about 0 weight percent to about 95 weight percent, said weight percents being based on the total weight of the ionically-modified silicone cross-polymer composition for the skin covering sheet. In one embodiment herein the lower endpoint of the aforementioned ranges can be any one of 0.1 weight percent, 0.5 weight percent, 1 weight percent, 5 weight percent and 10 weight percent.

Many types of previous metal catalysts, e.g., platinum catalysts are known and such platinum catalysts may be used for the hydrosilylation reaction in the present invention. When optical clarity is required the preferred platinum catalysts are those platinum compound catalysts that are soluble in the reaction mixture. The platinum compound can be selected from those having the formula ($PtCl_2Olefin$) and $H(PtCl_3Olefin)$ as described in U.S. Pat. No. 3,159,601, hereby incorporated by reference. A further platinum containing material usable in the compositions of the present invention is the cyclopropane complex of platinum chloride described in U.S. Pat. No. 3,159,662 hereby incorporated by reference. Further the platinum containing material can be a complex formed from chloroplatinic acid with up to 2 moles per gram of platinum of a member selected from the class consisting of alcohols, ethers, aldehydes and mixtures of the above as described in U.S. Pat. No. 3,220,972 hereby incorporated by reference. The catalysts most specifically used herein are described in U.S. Pat. Nos. 3,715,334; 3,775,452; and U.S. Pat. No. 3,814,730 to Karstedt. Additional background concerning the art may be found at J. L. Spier, "Homogeneous Catalysis of Hydrosilation by Transition Metals, in Advances in Organometallic Chemistry, volume 17, pages 407 through 447, F. G. A. Stone and R. West editors, published by the Academic Press (New York, 1979).

In one embodiment the precious metal catalysts that may be used herein, are such as the non-limiting examples of rhodium, ruthenium, palladium, osmium, iridium and platinum catalysts and combinations thereof.

In one embodiment herein the platinum catalyst is in a soluble complex form.

In one other embodiment, the platinum catalyst is selected from the group consisting of platinic chloride, chloroplatinic acid, bis(acetylacetonato)platinum, ($\eta^5$-Cyclopentadienyl) trialkylplatinum and combinations thereof.

Persons skilled in the art can easily determine an effective amount of precious metal catalyst. The catalyst can be present in a very wide range, but normally a range of from between 0.1 and 10,000 ppm, more specifically from between 1 and 100 ppm. In one embodiment herein the basis amount of the catalyst is based on the amount of ionically-modified silicone cross-polymer or the amounts of the respective components used to produce the ionically-modified silicone cross-polymer.

In one specific embodiment herein the steps (b) and (c) of the process(es) described herein can be conducted at a temperature of from about 0° C. to about 200° C., more specifically, from about 10° C. to about 150° C. and most specifically from about from about 20° C. to about 120° C., and at a pressure of from about 0.1 atm to about 10 atm, more specifically of from about 0.5 atm to about 5 atm and most specifically of from about 0.9 atm to about 2 atm.

In one specific embodiment herein the steps of the process(es) described herein (either separately or together) can be conducted for a period of from about 5 minutes to about 48 hours, more specifically from about 20 minutes to about 36 hours and most specifically from about 1 hour to about 12 hours.

In one embodiment the process of preparing an ionically-modified silicone cross-polymer composition for cosmetic compositions can further comprise the use of a hydrosilylation inhibitor, such as the non-limiting example of mercaptyl compounds. In one embodiment the inhibitor can be used during step (b) of the process of preparing an ionically-modified silicone cross-polymer composition for cosmetic compositions. Non-limiting examples of hydrosilylation inhibitors are described in U.S. Pat. Nos. 3,445,420, 4,256,870, 4,465,818, 4,562,096, and 5,629,387, the disclosures of which are hereby incorporated by reference. It is well within the skill in the art to select a suitable hydrosilylation inhibitor.

It will be understood herein that the respective R values, subscripts and other variables defined herein can have the same definitions in the process embodiments herein as these variables have in the composition embodiments described herein and vice-versa.

In one embodiment herein that the reaction of hydride-functional silicone (i) with olefin (ii) can be conducted under general hydrosilylation conditions which can comprises the use of an effective amount of precious metal catalyst (iii) such as those catalysts described herein, e.g., a platinum catalyst, and in the presence of a solvent (iv) and in conditions as described herein and/or as are known to those skilled in the art.

In one embodiment herein, it is to be noted that acetylene analogs of the olefin (ii) will react to form similar products. Thus, as used herein, the phrase an "olefin selected from non-silicones and organo-modified silicones with the general structure (V)", is intended to also include an acetylenically unsaturated molecule. The phrase "an acetylenically unsaturated molecule" means a molecule possessing one or more interior, pendant or terminal carbon-carbon triple bonds, i.e. a —C≡C— linkage.

The ionic silicon hydride (i) and vinyl (ii) functionalities can be made by a variety of techniques that are known in the art, such as those described in U.S. Pat. No. 8,697,829, the contents of which are incorporated by reference herein.

The non-ionic silicone olefins (ii) can be made by a variety of techniques that are known in the art. They are typically prepared by equilibration reactions of suitable monomers catalyzed by acids or bases.

The solvent (iv) when it is of the general formula (VI) can be made by a variety of techniques that are known in the art, such as those described in JP 6,247,827 and JP 6,247,835, the contents of which are incorporated by reference herein.

In one other embodiment herein there is provided a cosmetic compositions comprising a an oil phase and an aqueous phase which cosmetic composition is made by the process of adding at least one crosslinked ionic silicone network gel to the oil phase of the cosmetic composition and wherein the crosslinked ionic silicone network gel is formed by polymerizing
i) at least one oxirane-functionalized compound;
ii) an oxirane ring-opening polymerization catalyst;
iii) a solvent; and,
iv) optionally, one or more silicon hydride activators,
wherein at least one of (i), (iii) or (iv) comprises a silicone of formula (I) as described herein and wherein the crosslinked ionic silicone network is formed by the ring-opening polymerization of oxirane moiety with hydride moiety; and, shearing the crosslinked ionic silicone network during and/or after the polymerization step with at least solvent (as described herein) to form the crosslinked ionic silicone network gel.

In one embodiment herein the oxirane ring-opening polymerization catalyst is an acid catalyst capable of polymerizing an epoxy group.

In a more specific embodiment, the acid catalyst capable of polymerizing an epoxy group is selected from onium salt generated acids; metal salts selected from the group consisting of aluminum trichloride and ferric chloride; lanthium triflates; and, platinum compounds.

In one even more specific embodiment, the acid catalyst is a lanthium triflate of the general formula:

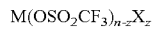

$$M(OSO_2CF_3)_{n-z}X_z$$

where M is the cation derived from a lanthanide and n is the valence of the lanthanide in the compound, X is an additional organic or inorganic salt residue (anionic residue), z is a number lower than n or 0.

The term "lanthanide" (M) shall be selected out of lanthanum and each of the chemical elements whose atomic number is between 58 (cerium) and 71 (lutetium), inclusive. In one specific embodiment, the lanthanide is selected from the group consisting of lanthan, ytterbium and samarium.

Some lanthanide triflates are commercial products or can be obtained by conventional, well-known methods. As X other organic and/or inorganic salt residues can be used, e.g., anions such as $Cl^-$, $Br^-$, $I^-$, $NO_3^-$, $HSO_4^-$, $H_2PO_3^-$, $HCO_3^-$, $CH_3COO^-$, $C_2H_5OO^-$, $C_6H_5COO^-$ which may form mixed salts with the lanthanide M.

Z is a number between 0 and n−1, so that at least one triflate residue is included in the lanthium triflate. More specifically the lanthium triflate is such that Z is 0 or 1, more specifically Z is 0. The lanthium triflate may comprise one or more metal ions M which may be the same or different.

In another embodiment herein the oxirane ring-opening polymerization-effective catalyst can be a platinum catalyst which operates under cationic cure conditions to ring-open the oxirane group of the oxirane silicone copolymer bearing ionic radicals. It will be understood herein that cationic polymerization conditions comprise any reaction parameters that provide for the ring-opening of the oxirane moiety with a silyl-hydride moiety.

Cationic polymerization conditions can be generated by addition of an acid catalyst capable of polymerizing an epoxy group such as, for example, by addition of onium salt generated acids and certain metal salts, such as, for example, aluminum trichloride and ferric chloride, which act as Lewis acids or by addition of lanthanide triflates, see PCT Int. Appl. WO 0008,087. Acid catalyzed polymerization of epoxides is a well known method of forming organic polymers and has been applied to epoxy-functional siloxane compounds in order to form siloxane polyalkyleneoxide block copolymers for use in a variety of applications as, for example, release coatings on paper, see, for example, U.S. Pat. No. 4,279,717, and in conjunction with organic materials to form coatings and modified plastic compositions, see for example, U.S. Pat. Nos. 5,354,796 and 5,663,752.

One precautionary note must be observed, that is if the cationic polymerization is conducted in the presence of cyclic siloxanes, e.g. $D_3$, $D_4$ or $D_5$ and the like, the strength of the acid catalysis employed must be such that cationic polymerization of the epoxide moiety occurs but polymerization of the cyclic siloxane does not occur to any appreciable extent.

In one embodiment the oxirane ring-opening polymerization catalyst can be any of the precious metal catalysts described herein.

In one other embodiment, the solvent can be any of the solvents described herein.

In yet a further embodiment the silicon hydride activator can be any of the Si—H containing compounds described herein.

The term "hydrophilic" is used to describe materials which are wetted by water (i.e. the surfaces of the materials have contact angles with water less than 90°. By contrast, the term "hydrophobic" is used to describe materials which are not wetted by water (i.e. the surfaces of hydrophobic materials have contact angles with water greater than 90°). While it is relatively straight forward to determine contact angle directed by optical measurements at the liquid-solid interface between water and flat solid surfaces, it is relatively complex to obtain contact angle between individual fibers or filaments in water. Yet these measurements may be accomplished utilizing a Wilhelmy balance principal. Relative hydrophilic/hydrophobic nature of individual fibers or filaments can be calculated through the fiber wettability values.

The content of cosmeceutical active in the cosmetic may be appropriately determined according to the type and purpose of use, but in too small an amount the effectiveness will be reduced, and therefore they are preferably added at 0.01% to 25%, more specifically at 0.1-20 wt % in the cosmetic. No particular problem results if the cosmeceutical active is in a supersaturated state or in a precipitated crystal state in the cosmetic. Cosmeceutical active ingredients may also be encapsulated together with absorption accelerators, or a retaining layer may be provided for the cosmeceutical active ingredients.

In one specific embodiment the amount of the crosslinked silicone network in the crosslinked silicone network gel can comprise from about 0.1% to about 90%, more specifically from about 1 to about 50%. The amount of the crosslinked silicone network gel that can be present in the oil phase of the cosmetic can be from about 0.1 to about 99 weight percent, more specifically from about 0.5 to about 50 weight percent.

The cosmetic composition according to the invention may also contain added absorption accelerators, dissolution aids or preventers, aromatic agents, and the like. The thickness of the application of the cosmetic on the skin is not particularly restricted. However, if it is too thin the cosmeceutical active ingredient content may be increased. In most cases, the thickness is preferably 10-200 μm.

In an embodiment of the invention, the cosmetic may be applied to a selected area of skin for a predetermined time ranging from 0.5 to 24 hours, preferably up to 8 hours and more preferably 4 hours per day. An intensive course of treatment may require at least a 3 month course of application for achieving a significant improvement in skin appearance.

Skin conditioners, moisturizers and surfactants may be included as cosmetically acceptable additives within the cosmetic. Illustrative conditioners include mineral oil, petrolatum, vegetable oils (such as soybean or maleated soybean oil), dimethicone, dimethicone copolyol, cationic monomers and polymers (such as distearyl dimethyl ammonium chloride). Illustrative moisturizers are polyols such as sorbitol, glycerin, propylene glycol, ethylene glycol, polyethylene glycol, polypropylene glycol, 1,3-butane diol, hexylene glycol, isoprene glycol, xylitol, fructose and mixtures thereof.

Surfactants may be those selected from the anionic, cationic, nonionic, amphoteric, zwitterionic and combinations thereof. Most preferred are nonionic and amphoteric surfactants due to their mildness.

Amounts of the conditioners, moisturizers and surfactants may each independently range from about 0.01 to about 45%, preferably from about 0.1 to about 30%, optimally from about 1 to about 20% by weight for each category based on the weight of the cosmetic.

In preferred embodiments of the present invention, the cosmeceutical active agents known in the art may be incorporated in the cosmetic for improving skin appearance. These agents can be any of anti-blotching, anti-aging, eye contour, slimming, soothing/sunburn, anti-irritating, skin firming and lifting, free radical scavengers, hydratives, vitamins and anti-oxidants and minerals.

The cosmetic can be used anywhere on the face or body skin to predetermined areas for delivery of ingredients. The cosmetic will have sufficient spreadability and flexibility, to conform to the desired treatment area of the user's skin. In a particularly preferred, but not necessary, embodiment of the present invention, the cosmetic is a facial mask adapted to conform to facial features.

Suitable skin benefit agents can be used in the present invention include, but are not limited to: anti-wrinkle or skin-tightening agents; anti-aging agents; moisturizing agents; skin-whitening or depigmentation agents; anti-inflammatory agents; anti-acne agents; stretch-mark/scar removing agents; dark circle reduction agents; and, antioxidants.

The cosmetic may also comprise a gel, such as a hydrogel, comprised of, for example, agarose or a water-soluble low-substituted cellulose ether which may include methyl cellulose, hydroxyethyl cellulose, hydroxypropyl cellulose, hydroxypropylmethyl cellulose, hydroxypropylhydroxyethyl cellulose, hydroxyethylmethyl cellulose, ethyl cellulose, hydroxyethylethyl cellulose, or carboxymethyl cellulose. In a preferred but not necessary embodiment of the present invention, the cosmetic is completely water-soluble, so upon application of water or like liquid activator, the cosmetic softens and conforms to the skin, and subsequently, the cosmetic is absorbed by the skin surface without having to be removed.

The cosmetic according to the invention may be, in particular, W/O or O/W skin creams, day and night creams, eye creams, face creams, antiwrinkle creams, moisturizing creams, bleaching creams, vitamin creams, skin lotions, care lotions and moisturizing lotions.

It is understood herein that the various descriptive support provided in the respective embodiments described herein applies equally and interchangeably to all portions and embodiments of the specification. Thus, it is understood herein that the respective R definitions, subscript values and other variables defined herein with regard to one embodiment, can have the same definitions with regard to the description section in another embodiment, as well as the process embodiments herein, and also in any other way these variables have been described elsewhere in the composition or process embodiments described herein, and vice-versa.

It will be understood herein that any reference to cosmetic compositions, emulsions, applications and ingredients are in regard to their presence in one non-limiting embodiment as a component(s) of a cosmetic application as described herein.

In one embodiment herein, the cosmetic compositions of the present invention are self-emulsifying.

In another embodiment herein, the crosslinked ionic silicone network gel, the oil phase of the cosmetic composition and the overall cosmetic composition or application thereof described herein may be further processed under low to high shear to adjust the viscosity and sensory feel of the composition. This may be achieved, for example, by subjecting the composition to a moderate to high shearing force. High shear may be applied using, for example, a Sonolator apparatus, a Gaulin Homogenizer or a Micro Fluidizer apparatus. Optionally, one or more carrier solvent may be added to the silicone composition prior to the shearing.

In a specific embodiment, the cosmetic composition of the present invention is a solid, typically having a creamy consistency, wherein the ionically-modified silicone cross-polymer acts as a means for gelling the fluid to reversibly impart characteristics of a solid to the fluid. At rest, the cosmetic composition exhibits the properties of a solid gel material. The cosmetic composition of the present invention exhibits high stability and resistance to syneresis, that is, the composition exhibits little or no tendency for fluid to flow from the composition and imparts high stability and syneresis resistance to cosmetic compositions which include the ionically-modified silicone cross-polymer as a component. The high stability and syneresis resistance persists with prolonged aging of such ionically-modified silicone cross-polymer and cosmetic compositions. However, solvent may be released from the ionically-modified silicone cross-polymer by subjecting the cosmetic composition to a shearing force, such as, for example, by rubbing the composition between one's fingers, to provide improved sensory feel characteristic of the fluid component of the silicone material.

Water (or a water equivalent such as a non-aqueous hydroxylic solvent), siloxane, linear or cyclic, or lipophilic fluid (oil swelling agent, oil swellable) may be used as the solvent which may function as a swelling agent. Lipophilic fluids suitable for use as the solvent component of the composition of the present invention are those described herein. In a preferred embodiment, the solvent component of the composition of the present invention exhibits a viscosity of below about 1,000 cSt, preferably below about 500 cSt, more preferably below about 250 cSt, and most preferably below 100 cSt, at 25° C.

In one preferred embodiment, the cross-polymer is an ionically-modified silicone cross-polymer that is insoluble in various fluid components, but that is capable of being swollen by the solvent. The amount of crosslinking present in the ionically-modified silicone cross-polymer may be characterized with respect to the degree of swelling exhibited by the cross-polymer in the solvent.

In another specific embodiment, the cross linked structure of the ionically-modified silicone cross-polymer is effective to allow the cross-polymer to be swollen by a low molecular weight silicone fluid, such as, for example, decamethylcyclopentasiloxane, from its original volume to a swollen volume as stated above.

The ionically-modified silicone cross-polymer of the present invention may be utilized as prepared or as the silicone component in cosmetic emulsions for use in cosmetic applications. As is generally known, emulsions comprise at least two immiscible phases one of which is continuous and the other which is discontinuous. In one embodiment herein, the non-miscible phases (immiscible phases) can be selected from the group consisting of aqueous, non-aqueous, and solid particulates.

Further emulsions may be liquids with varying viscosities or solids. Additionally, the particle size of the emulsions may render them microemulsions, and when sufficiently small, microemulsions may be transparent. Further it is also possible to prepare emulsions of emulsions and these are generally known as multiple emulsions. These emulsions may be: 1) aqueous emulsions where the discontinuous phase comprises water and the continuous phase comprises the cross linked ionic silicone network of the present invention; 2) aqueous emulsions where the discontinuous phase comprises the ionically-modified silicone cross-polymer of the present invention and the continuous phase comprises water; 3) non-aqueous emulsions where the discontinuous phase comprises a non-aqueous hydroxylic solvent and the continuous phase comprises the ionically-modified silicone cross-polymer of the present invention; and 4) non-aqueous emulsions where the continuous phase comprises a non-aqueous hydroxylic organic solvent and the discontinuous phase comprises the ionically-modified silicone cross-polymer of the present invention.

In one embodiment herein, the ionically-modified silicone cross-polymer is compatible with a particulate additive. In another more specific embodiment, the particulate additive is selected from inorganic particulates, polymeric latexes, and pigments.

As used herein the term "non-aqueous hydroxylic organic compound" or "non-aqueous hydroxylic solvent" means hydroxyl containing organic compounds exemplified by alcohols, glycols, polyhydric alcohols and polymeric glycols and mixtures thereof that are liquid at room temperature, e.g. about 25° C., and about one atmosphere pressure, and are used interchangeably with the term "solvent" as the same component. The non-aqueous organic hydroxylic solvents are selected from the group consisting of hydroxyl containing organic compounds comprising alcohols, glycols, polyhydric alcohols and polymeric glycols and mixtures thereof that are liquid at room temperature, e.g. about 25° C., and about one atmosphere pressure. Preferably the non-aqueous hydroxylic organic solvent is selected from the group consisting of ethylene glycol, ethanol, propyl alcohol, isopropyl alcohol, propylene glycol, dipropylene glycol, tripropylene glycol, butylene glycol, iso-butylene glycol, methyl propane diol, glycerin, sorbitol, polyethylene glycol, polypropylene glycol mono alkyl ethers, polyoxyalkylene copolymers and mixtures thereof.

Once the desired form is attained whether as a silicone only phase, an anhydrous mixture comprising the silicone phase, a hydrous mixture comprising the silicone phase, a water-in-oil emulsion, an oil-in-water emulsion, or either of the two non-aqueous emulsions or variations thereon, the resulting material is usually a high viscosity cream with good feel characteristics, and high absorbance of volatile siloxanes. It is capable of being blended into cosmetic formulations for hair care, skin care, and the like. In one embodiment herein, the crosslinked ionic silicone network can bind and slow release cosmeceutical actives.

In one embodiment the cosmetic composition described herein can contain further cosmetic components selected from the group consisting of deodorants, antiperspirants, antiperspirant/deodorants, shaving products, skin lotions, moisturizers, toners, bath products, cleansing products, hair care products such as shampoos, conditioners, mousses, styling gels, hair sprays, hair dyes, hair color products, hair bleaches, waving products, hair straighteners, manicure products such as nail polish, nail polish remover, nail creams and lotions, cuticle softeners, protective creams such as sunscreen, insect repellent and anti-aging products, color cosmetics such as lipsticks, foundations, face powders, eye liners, eye shadows, blushes, makeup, mascaras and other personal care formulations where silicone components have been conventionally added, as well as drug delivery systems for topical application of medicinal compositions that are to be applied to the skin.

In a more specific embodiment, the cosmetic application components of the present invention further comprises one or more cosmetic ingredients. Suitable cosmetic ingredients include, for example, emollients, moisturizers, humectants, pigments, including pearlescent pigments such as, for example, bismuth oxychloride and titanium dioxide coated mica, colorants, fragrances, biocides, preservatives, antioxidants, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, silicone oils, organic oils, waxes, film formers, thickening agents such as, for example, fumed silica or hydrated silica, particulate fillers, such as for example, talc, kaolin, starch, modified starch, mica, nylon, clays, such as, for example, bentonite and organo-modified clays.

Suitable cosmetic compositions are made by combining, in a manner known in the art, such as, for example, by mixing, one or more of the above components with ionically-modified silicone cross-polymer composition.

Suitable cosmetic compositions may be in the form of a single phase or in the form of an emulsion, including oil-in-water, water-in-oil and anhydrous emulsions where the silicone phase may be either the discontinuous phase or the continuous phase, as well as multiple emulsions, such as, for example, oil-in water-in-oil emulsions and water-in-oil-in water-emulsions; such as is described above.

In one useful embodiment, an antiperspirant composition comprises the cosmetic of the present invention and one or more active antiperspirant agents. Suitable antiperspirant agents include, for example, the Category I active antiperspirant ingredients listed in the U.S. Food and Drug Administration's Oct. 10, 1993 Monograph on antiperspirant drug products for over-the-counter human use, such as, for example, aluminum halides, aluminum hydroxyhalides, for example, aluminum chlorohydrate, and complexes or mixtures thereof with zirconyl oxyhalides and zirconyl hydroxyhalides, such as for example, aluminum-zirconium chlorohydrate, aluminum zirconium glycine complexes, such as, for example, aluminum zirconium tetrachlorohydrex gly.

In another useful embodiment, a skin care cosmetic composition comprises the ionically-modified silicone cross-polymer, and a vehicle, such as, for example, a silicone oil or an organic oil. The skin care composition may, optionally, further include emollients, such as, for example, triglyceride esters, wax esters, alkyl or alkenyl esters of fatty acids or polyhydric alcohol esters and one or more the known components conventionally used in skin care compositions, such as, for example, pigments, vitamins, such as, for example, Vitamin A, Vitamin C and Vitamin E, sunscreen or sunblock compounds, such as, for example, titanium dioxide, zinc oxide, oxybenzone, octylmethoxy cinnamate, butylmethoxy dibenzoylmethane, p-aminobenzoic acid and octyl dimethyl-p-aminobenzoic acid.

In another useful embodiment, a color cosmetic composition, such as, for example, a lipstick, a makeup or a mascara composition comprises the contents of the cosmetic composition herein, e.g., crosslinked ionic silicone network, and a coloring agent, such as a pigment, a water soluble dye or a liposoluble dye.

In another useful embodiment, the cosmetic compositions of the present invention are utilized in conjunction with fragrant materials. These fragrant materials may be fragrant compounds, encapsulated fragrant compounds or fragrance releasing compounds that either the neat compounds or are encapsulated.

It will be understood herein that the ionically-modified silicone cross-polymer composition for cosmetic compositions, such as the ionically-modified silicone cross-polymer composition made by the process(es) described herein, can be such that there are no polyether crosslinks in the ionically-modified silicone cross-polymer.

EXAMPLES

Example 1: Preparation of Ionically Modified (Sulfonate) Silicone Composite 0.21 parts by weight of C-30 alpha olefin (from Chevron Phillips Company), 48.78 parts by weight vinyl end capped polydimethyl-co-methyl-2-methylpropylphenylsulfonate siloxane with 0.062 mmol·g−1 vinyl and 0.328 mmol·g−1 sulfonate available from Momentive Performance Materials, and 150 parts by weight of decamethylpentacyclosiloxane were placed in a Ross mixer. The mixture was stirred, and heated to 80° C. till C-30 alpha olefin dissolved completely. Subsequently, the mixture was cooled down to 35° C., 1.02 parts by weight of a silanic hydrogen fluid represented by the average composition formula: $(CH_3)_3SiO((CH_3)_2SiO)_{20}((CH_3)HSiO)_{10}Si(CH_3)_3$ and 0.10 parts by weight of a Karstedt's catalyst containing 2% Platinum metal were added thereto and stirred till uniform mixture was obtained. Then, the mixture was stirred at 35° C. for 15 minutes to facilitate hydrosilylation giving solid cross-linked material, mixing was continued for another 45 minutes. Temperature was ramped to 80° C. and the solid material was mixed for 2 hours to ensure complete cross-linking/hydrosilylation. The solid polymer content of the cross linked material was found to be between 24-26%.

20 parts by weight of the above described cross-linked material containing 25% solid was blended with 80 parts by weight of decamethylpentacyclosiloxane in Silverson mixer for 5 minutes at 5000 rpm. The material obtained was additionally subjected to a 5 minute blending cycle at 5000 rpm 4 times. The swelled material was then passed through a Microfluidizer three times to get a smooth, silky gel containing ~5% solid-viscosity 6,600 cps.

Example 2: Preparation of Ionically Modified (Carboxylate) Silicone Composite 151.25 parts by weight vinyl end capped polydimethylsiloxane with 0.05 mmol·g−1 vinyl, and 900 parts by weight of Silsoft DML (a low molecular weight linear dimethicone fluid with a narrow chain length, available from Momentive Performance Materials) were placed in a Ross mixture. The mixture was stirred, and heated to 35° C. Subsequently, 3.53 parts by weight of a silanic hydrogen fluid represented by the average composition formula: $(CH3)3SiO((CH3)2SiO)20((CH3)HSiO)10Si(CH3)3$, 3.32 parts by weight of 10-undecenoic acid trimethylsilyl ester (UDA-E), and 0.50 parts by weight of a Karstedt's catalyst containing 2% Platinum metal were added thereto and stirred till uniform mixture was obtained. Then, the mixture was stirred at 35° C. for 15 minutes to facilitate hydrosilylation giving cross-linked material, mixing was continued for another 45 minutes. Temperature was ramped to 80° C. and the solid material was mixed for 4 hours to ensure complete cross-linking/hydrosilylation. The 10-undecenoic acid trimethylsilyl ester (UDA-E) contains an unsaturated group on one end, which is hydrosilylated, and a protected carboxylic acid on the other end. Afterwards, 20 parts by weight of water was added and the mixing was continued for another 2 hours. When the material is exposed to water, the acid is deprotected. The solid polymer content of the cross linked material was found to be between 14.5-15%. 200 parts by weight of the above described cross-linked material containing 15% solid was blended with 100 parts by weight of Silsoft DML in Silverson mixer for 5 minutes at 5000 rpm. The material obtained was additionally subjected to a 5 minute blending cycle at 5000 rpm 4 times. The swelled material was then passed through a Microfluidizer three times to get a smooth, silky gel containing ~10% solid-viscosity 36900 cps.

Example 3: Preparation of Ionically Modified (Sulfonate) Silicone Composite 16.27 parts by weight of C-30 alpha olefin (from Chevron Phillips Company), 243.9 parts by weight vinyl end capped polydimethyl-co-methyl-2-methylpropylphenylsulfonate siloxane with 0.062 mmol·g−1 vinyl and 0.328 mmol·g−1 sulfonate available from Momentive Performance Materials, and 1500 parts by weight of dimethicone-5cst were placed in a Ross mixer. The mixture was stirred, and heated to 80° C. till C-30 alpha olefin dissolved completely. Subsequently, the mixture was cooled down to 35° C., 7.05 parts by weight of a silanic hydrogen fluid represented by the average composition formula: $(CH_3)_3SiO((CH_3)_2SiO)_{20}((CH)HSiO)_{10}Si(CH_3)_3$ and 0.50 parts by weight of a Karstedt's catalyst containing 2% Platinum metal were added thereto and stirred till uniform mixture was obtained. Then, the mixture was stirred at 35° C. for 15 minutes to facilitate hydrosilylation giving solid cross-linked material, mixing was continued for another 45 minutes. Temperature was ramped to 80° C. and the solid material was mixed for 4 hours to ensure complete cross-linking/hydrosilylation. The solid polymer content of the cross linked material was found to be between 14.5-15%.

200 parts by weight of the above described cross-linked material containing 15% solid was blended with 100 parts by weight of decamethylpentacyclosiloxane in Silverson mixer for 5 minutes at 5000 rpm. The material obtained was additionally subjected to a 5 minute blending cycle at 5000 rpm 4 times. The swelled material was then passed through a Microfluidizer three times to get a smooth, silky gel containing 10% solid-viscosity 27700 cps.

Cosmetic Formulations Prepared Using Ionically Modified Silicone Composite (Sunscreen Lotion):

| Part | Ingredient | Wt % | Source |
|---|---|---|---|
| A | Silsoft 034 | 3 | Momentive Performance Materials |
| | SR 1000 (50%) | 1 | Momentive Performance Materials |
| | Example 1 | 20 | |
| | PEG-100 Glycerol Stearate | 3 | BASF |
| | Stearyl Alcohol | 1.5 | |
| | Stearic Acid | 1 | |
| | Cetiol B (Dibutyl Dipate) | 0.6 | BASF |
| | Benzophhenone-3 (2-Hydroxy-4-Methoxybenzophenone) | 2.0 | |
| | Avobenzene (Eusolex 9020) | 1.5 | Merck |
| B | Demineralized Water | 51.68 | |
| | Carbopol U21 | 0.1 | Lubrizol |
| | Glycerin | 2.0 | |
| C | Triethanolamine | 0.1 | |
| D | Demineralized Water | 5.12 | |
| | Niacinamide | 2.0 | |
| E | Panthanol | 1 | |
| | Preservative | 0.1 | |
| | Tocopherol Acetate | 0.3 | |

Procedure:

i. PART A; Premix Silsoft 034 and SR 1000 in a main vessel; add remaining ingredients of PART A, ii. Heat Part A up to 75° C., under stirring, iii. Part B: in a separate vessel add Carbopol U21 in given amount of water, after dispersion, allow it to wet then mix well: add glycerin and mix well, iv. Heat Part B up to 75° C., under stirring, v. At 75° C., Add Part B in to Part A with high speed stirring, stir well for 5 min, vi. Add PART C into PART AB and mix well for 5 min, vii. Cool the batch the under stirring up to 50° C., viii. Premix Part D in a separate vessel, add it in to PART ABC and mix well, ix. Add PART E ingredients as per given order and mix well after each addition, and x. Mix the batch for 5 to 8 min. and finish the process.

Liquid Foundation:

| Part | Ingredient | Wt % | Source |
|---|---|---|---|
| A | Example 1 | 5 | |
| | D5 | 10 | Momentive |
| | SF 1540 | 4 | Momentive |
| | Crodamol GTCC | 4 | Croda |
| B | Pigment | 6 | |
| | Tospearl 2000B | 2 | Momentive |
| C | Water | 64 | |
| | NaCl | 1 | |
| | SF 1188A | 1 | Momentive |
| | Glycerin | 3 | |

Procedure:

i. Mix all ingredients of phase A, homogenize, ii. Mix all ingredients of phase B, and to phase A, and iii. Mix all ingredients of phase C and add to the above mixture slowly.

Anti-Acne Moisturizing Cream:

| Phase | Ingredient | Control gel | Example 1 gel | Source |
|---|---|---|---|---|
| A | Water | 64 | 64 | |
| | Glycerin | 4 | 4 | |
| | NaCl | 1 | 1 | |
| B | Isopropyl myristate | 5 | 5 | |
| | Silsoft 034 | 1 | 1 | Momentive |
| | D5 | 7 | 7 | Momentive |
| | SF 1540 | 2 | 2 | Momentive |
| | Example 1 | 0 | 10 | Momentive |
| | Silsoft Silicone Gel | 10 | 0 | Momentive |
| C | Water | 4 | 4 | |
| | Niacinamide | 5 | 2 | |

Procedure:

i. Dissolve Niacinamide in water (Phase C), ii. Mix all ingredients of Phase A, & add Phase C to it (water phase), iii. Mix all ingredients of Phase B, homogenize in Silverson mixer at 3000 rpm for 3 min (oil phase), and iv. Under stirring add water phase to oil phase (phase B) drop-wise at 200 rpm, further mix for 10 min.

Salicylic Acid Containing Cream:

| Phase | Ingredient | Control Gel | Example 2 | Source |
|---|---|---|---|---|
| A | SF-1202 | 1 | 6 | Momentive |
| | Liquid paraffin | 4 | 4 | Rankem |
| | Caprylic/Capric Triglyceride | 4 | 4 | Croda |
| | Control gel | 10 | 0 | Momentive |
| | Example 2 | 0 | 5 | Momentive |
| | Silsoft 1000 | 7 | 2 | Momentive |
| | Euxyl 9010 | 0.5 | 0.5 | Schülke&Mayr |
| B | Salicylic acid | 2 | 2 | Sigma-Aldrich |
| | Glycerin | 2 | 2 | Rankem |
| | Dipropylene Glycol | 6 | 6 | Rankem |
| | Water | 68.5 | 68.5 | |
| | Total | 100 | 100 | |

Procedure:

i. Mix all ingredients of phase A and homogenize using homogenizer for 5-10 mins, ii. Mix all ingredients of phase B except water, iii. Add water drop-wise to phase A being mixed at 25° C., @600 rpm with stirrer, and
iv. Add Phase B to above mixture drop-wise with stirring.

Dexapanthenol Containing Cream:

| Phase | Ingredient | Control Gel | Example 2 | Source |
|---|---|---|---|---|
| A | SF-1202 | 1 | 6 | Momentive |
| | Liquid paraffin | 4 | 4 | Rankem |
| | Caprylic/Capric Triglyceride | 4 | 4 | Croda |
| | Control gel | 10 | 0 | Momentive |
| | Example 2 | 0 | 5 | Momentive |
| | Silsoft 1000 | 2 | 2 | Momentive |
| | Euxyl 9010 | 0.5 | 0.5 | Schülke&Mayr |
| B | Dexapanthenol | 2 | 2 | Sigma-Aldrich |
| | Glycerin | 2 | 2 | Rankem |
| | Dipropylene Glycol | 3 | 3 | Rankem |
| | Water | 71.5 | 71.5 | |
| | Total | 100 | 100 | |

Procedure:
i. Mix all ingredients of Phase A and homogenize using homogenizer for 5-10 mins, and
ii. Mix all ingredients of Phase B and add drop-wise to Phase A with stirring.

Arbutin Containing Cream:

| Phase | Ingredient | Control Gel | Example 3 | Source |
|---|---|---|---|---|
| A | SF-1202 | 1 | 6 | Momentive |
| | Liquid paraffin | 4 | 4 | Rankem |
| | Caprylic/Capric Triglyceride | 4 | 4 | Croda |
| | Control gel | 10 | 0 | Momentive |
| | Example 3 | 0 | 5 | Momentive |
| | Silsoft 1000 | 2 | 2 | Momentive |
| | Euxyl 9010 | 0.5 | 0.5 | Schülke&Mayr |
| B | Arbutin | 2 | 2 | |
| | Glycerin | 2 | 2 | Rankem |
| | Dipropylene Glycol | 3 | 3 | Rankem |
| | Water | 71.5 | 71.5 | |
| | Total | 100 | 100 | |

Procedure:
i; Mix all ingredients of Phase A and homogenize using homogenizer for 5-10 mins, and
ii. Mix all ingredients of Phase B and add drop-wise to Phase A with stirring.

In-Vitro Niacinamide Release Testing:

Typically, 100 mg of a control/example 1 formulation was spread evenly over a synthetic inert support membrane having 450 nm diameter pores. The membrane was placed in a Franz diffusion cell in such a way that the side on which formulation was applied faces upwards while other side of the membrane is in direct contact with the receiver medium, water. The release rate experiment was carried out at 22±1° C. Samples (~0.4 mL) were withdrawn from the receiver medium at predetermined time intervals 15, 30, 60, 90, 120 & 180 mins, and the volume sampled was replaced with fresh receptor medium (water). Sink condition was achieved by selecting a receiver medium with a high capacity to dissolve the active-niacinamide. Typically, the receiver medium and amount of sample applied decided so that the active concentration does not exceed 10-20% of the active solubility in receptor medium at the end of the release test. The tests were done in duplicate, and the average of two release tests at particular time point was plotted against the time. Niacinamide was quantified using reversed phase HPLC (C18 column). Niacinamide release was monitored with UV detector at 260 nm using Acetonitrile-Water-IPA mobile phase. Under this method, Niacinamide eluted at 2.5 min.

Table 1 shows the average % Niacinamide released from control & example-1 formulation at given time.

TABLE 1

| Time (mins) | Control formlation (% Niacinamide released) | Example-1 formulation (% Niacinamide released) |
|---|---|---|
| 15 | 31 | 39 |
| 30 | 39 | 50 |
| 60 | 52 | 57 |
| 90 | 53 | 59 |
| 120 | 53 | 58 |
| 180 | 60 | 60 |

FIG. 1 is a graph illustrating the % release of Niacinamide from the control & example-1 formulation.

Based on the release profile it is clear that example-1 formulation which contains ionically modified silicone released Niacinamide faster than the control formulation prepared using Silsoft silicone gel, which does not have any ionic groups.

To further understand the difference in interaction between ionically modified silicone and control/Silsoft silicone gel, differential scanning calorimetry (DSC) studies were carried out on pure active-niacinamide, and its blends with silsoft silicone and ionically modified silicone. 2% Niacinamide blends were prepared by thoroughly mixing Niacinamide with above silicones using spatula followed by high-speed mixing in Flack-Tek for 5 minutes. The free Niacinamide and Niacinamide loaded Silsoft silicone gel and ionically modified silicone were subjected to a heating and cooling cycle under nitrogen atmosphere. The DSC thermograms are show in FIG. 2.

Figure 2:
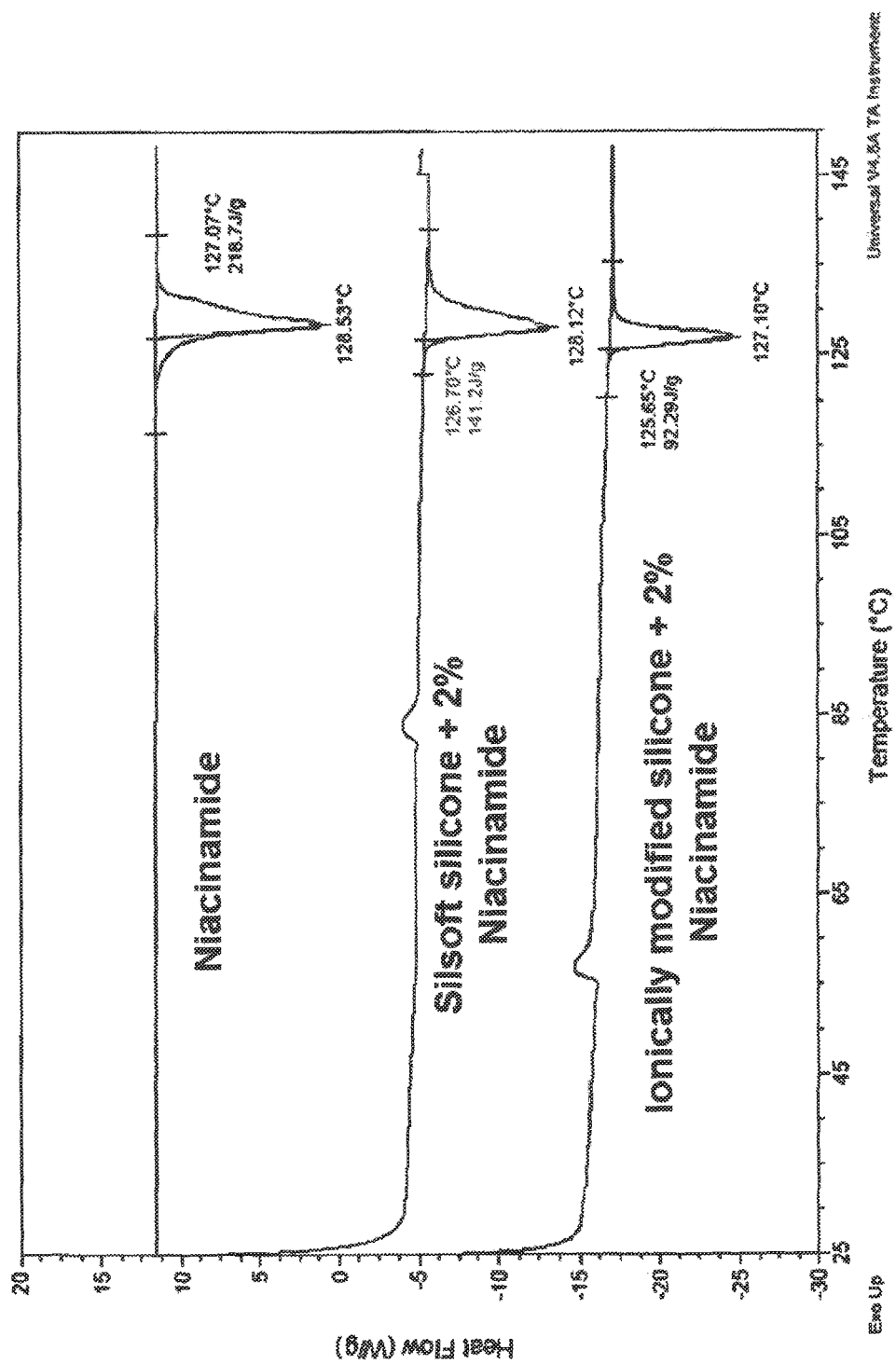
FIG. 2 shows the DSC thermogram for pure niacinamide and its blends with Silsoft silicone and ionically modified silicone.

FIG. 2 shows the DSC thermogram for pure niacinamide and its blends with Silsoft silicone and ionically modified silicone.

Table 2 shows the % crystalline Niacinamide in blends of Silsoft silicone and ionically modified silicone. ΔH is a heat change associated with the melting of Niacinamide.

TABLE 2

| Sample Name | ΔH (J/g) | % Crystallinity |
|---|---|---|
| Niacinamide | 218.7 | 100 |
| Silsoft silicone + 2% niacinamide | 140 | 64 |
| Ionically modified silicone + 2% niacinamide | 93 | 43 |

From Table 2 it is clear that Niacinamide interacts with ionically modified silicone strongly, exhibiting less crystalline portion. In other words we can say that Niacinamide is more compatible with ionically modified silicone and therefore shown more amorphous Niacinamide content than the Silsoft silicone.

In-Vitro Salicylic Acid & Dexapanthenol Release Testing:

Typically, 200 mg of a control/example 2 formulations were spread evenly over a dull side of a synthetic inert support membrane (Milipore Express Plus® membrane) having 220 nm diameter pores. The membrane was placed in a Franz diffusion cell in such a way that the side on which formulation was applied faces upwards while other side of the membrane is in direct contact with the receiver medium, PBS pH 7.4 containing 135 μM NaCl. The release rate experiment was carried out at 22±1° C. Samples (~0.4 mL) were withdrawn from the receiver medium at predetermined time intervals 30, 60, 90, 120, 180 & 360 mins, and the volume sampled was replaced with fresh receptor medium (PBS pH 7.4 containing 135 μM NaCl). Sink condition was achieved by selecting a receiver medium with a high capacity to dissolve the actives-salicylic acid and Dexapanthenol. Actives were quantified using reversed phase HPLC (C18 column). Salicylic acid release was monitored with UV detector at 300 nm using Acetonitrile-Water-IPA mobile phase. Under this method, salicylic acid eluted at 4.6 min. Dexapanthenol release was monitored with UV detector at 206 nm using Acetonitrile-Water-IPA mobile phase. Under this method, Dexapanthenol eluted at 4.9 min.

Table 3 shows the % Salicylic acid released from control & example-2 formulation at given time.

TABLE 3

| Time (mins) | Control formulation (% Salicylic acid released) | Example-2 formulation (% Salicylic acid released) |
|---|---|---|
| 30 | 51.91 | 35.81 |
| 60 | 65.79 | 70.98 |
| 90 | 71.53 | 70.61 |
| 120 | 66.81 | 72.97 |
| 180 | 71.86 | 76.27 |
| 360 | 69.27 | 73.72 |

Figure 3:
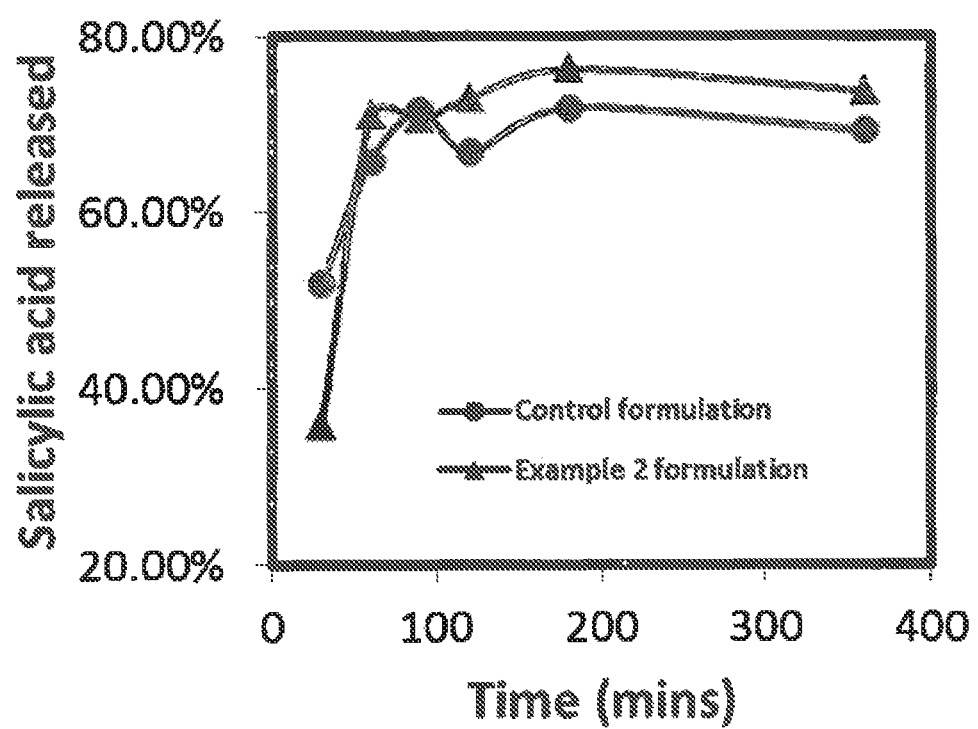
FIG. 3 is a graph illustrating the % release of salicylic acid from the control & example-2 formulation.

FIG. 3 is a graph illustrating the % release of salicylic acid from the control & example-2 formulation.

Table 4 shows the % Dexapanthenol released from control & example-2 formulation at given time.

TABLE 4

| Time (mins) | Control formulation (% Dexapanthenol released) | Example-2 formulation (% Dexapanthenol released) |
|---|---|---|
| 30 | 14.92 | 9.37 |
| 60 | 19.42 | 22.08 |
| 90 | 22.72 | 22.42 |
| 120 | 22.42 | 22.31 |
| 180 | 26.0 | 27.52 |
| 360 | 28.42 | 28.42 |

Figure 4:
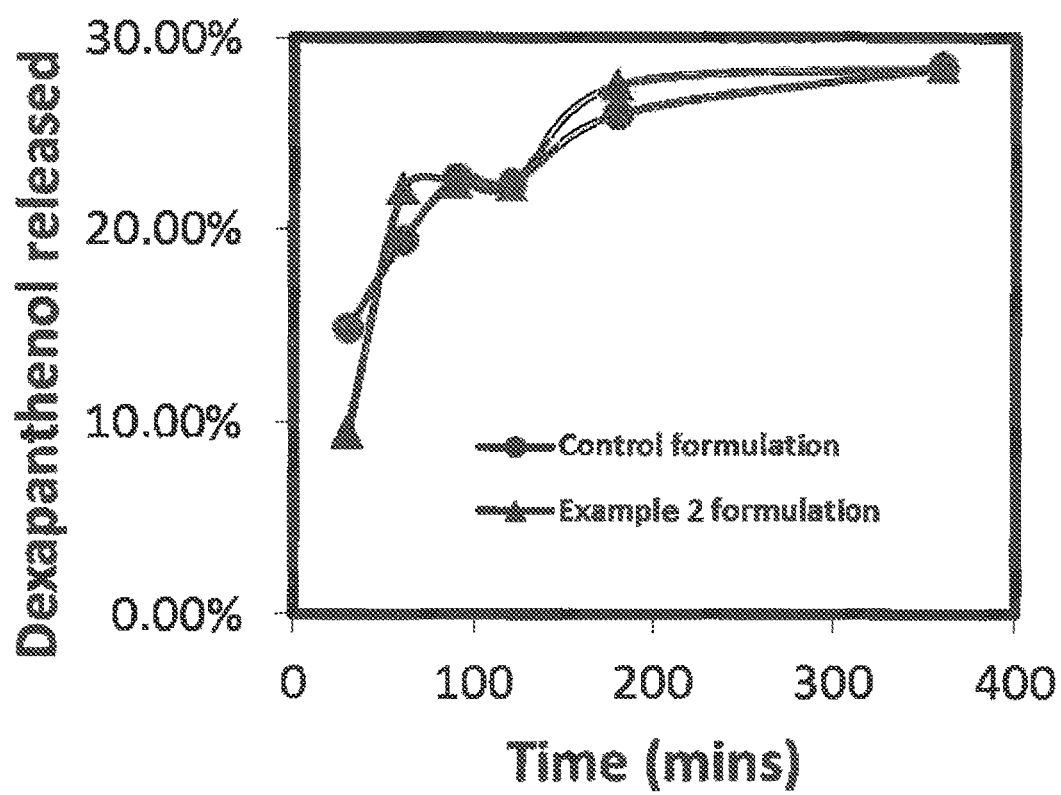
FIG. 4 is a graph illustrating the % release of dexapanthenol from the control & example-2 formulation.

FIG. 4 is a graph illustrating the % release of dexapanthenol from the control & example-2 formulation.

In-vitro Arbutin release Testing:

Typically, 200 mg of a control/example 3 formulations were spread evenly over a dull side of a synthetic inert support membrane (Milipore Express Plus® membrane) having 220 nm diameter pores. The membrane was placed in a Franz diffusion cell in such a way that the side on which formulation was applied faces upwards while other side of the membrane is in direct contact with the receiver medium, PBS pH 7.4 containing 135 μM NaCl for Arbutin and PBS pH 7.4 containing 135 uM NaCl and 2% PEG300. The release rate experiment was carried out at 22-1° C. Samples (~0.4 mL) were withdrawn from the receiver medium at predetermined time intervals 30, 60, 90, 120, 180 & 360 mins, and the volume sampled was replaced with fresh receptor medium. Sink condition was achieved by selecting a receiver medium with a high capacity to dissolve the actives-Arbutin and caffeine. Actives were quantified using reversed phase HPLC (C18 column). Arbutin release was monitored with UV detector at 280 nm using Acetonitrile-Water-IPA mobile phase. Under this method, arbutin eluted at 2.3 min. Caffeine release was monitored with UV detector at 243 nm using Acetonitrile-Water-IPA mobile phase. Under this method, caffeine eluted at 10.3 min.

Table 5 shows the % Arbutin released from control & example-3 formulation at given time.

TABLE 5

| Time (mins) | Control formulation (% Arbutin released) | Example-2 formulation (% Arbutin released) |
|---|---|---|
| 30 | 4.23 | 8.51 |
| 60 | 5.25 | 9.93 |
| 90 | 6.45 | 9.37 |
| 120 | 7.46 | 11.47 |
| 180 | 8.43 | 13.01 |
| 360 | 9.37 | 14.18 |

Figure 5:
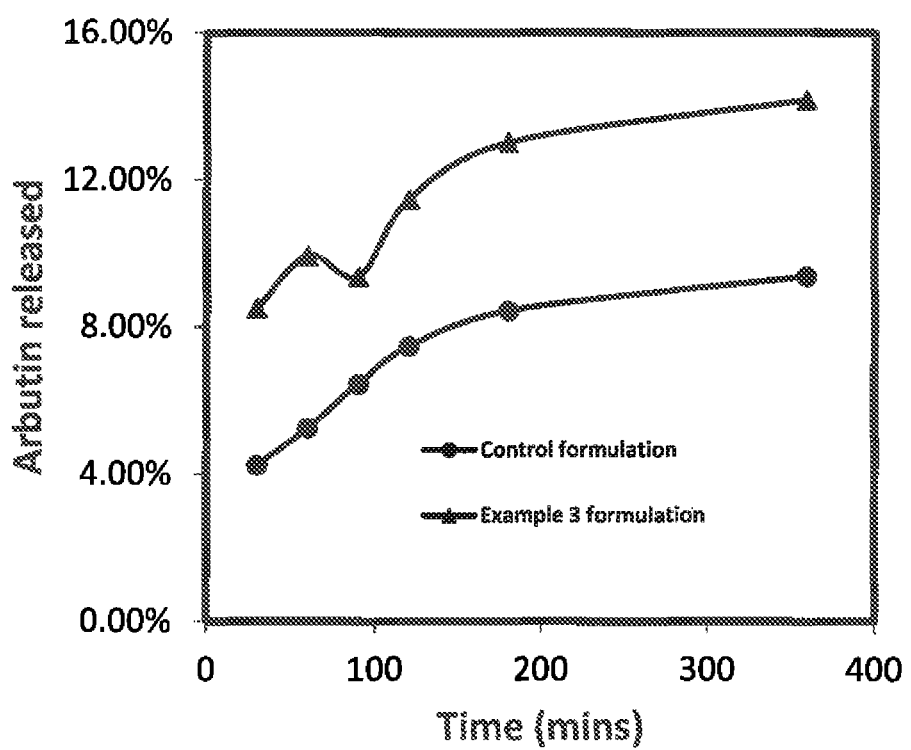
FIG. 5 is a graph illustrating the % release of arbutin from the control & example-3 formulation.

FIG. 5 is a graph illustrating the % release of arbutin from the control & example-3 formulation.

The above noted examples clearly demonstrate that all of the ionic silicone based compositions have shown significant improvement over traditional non-ionic silicone based composition with respect to the compatibility with hydrophilic and lipophilic ingredients, pigment dispersion and sensory feeling.

While the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention but that the invention will include all embodiments falling within the scope of the appended claims.

The invention claimed is:

1. A method of preparing a cosmetic composition comprising an oil phase and optionally an aqueous phase wherein the method comprising
   (a) reacting
      i) at least one silicone hydride bearing at least two Si—H residues,
      ii) at least one cross-linker silicone with two or more Si-unsaturated radicals,
   wherein at least one of (i) or (ii) silicone is an ionic silicone having the general formula (I):

$$M^1{}_a M^2{}_b M^3{}_c D^1{}_d D^2{}_e D^3{}_f T^1{}_g T^2{}_h T^3{}_i Q_j \quad (I)$$

wherein:
$M^1 = R^1 R^2 R^3 SiO_{1/2}$
$M^2 = R^4 R^5 R^6 SiO_{1/2}$
$M^3 = R^7 R^8 R^9 SiO_{1/2}$
$D^1 = R^{10} R^{11} SiO_{2/2}$
$D^2 = R^{12} R^{13} SiO_{2/2}$
$D^3 = R^{14} R^{15} SiO_{2/2}$
$T^1 = R^{16} SiO_{3/2}$
$T^2 = R^{17} SiO_{3/2}$
$T^3 = R^{18} SiO_{3/2}$
$Q = SiO_{4/2}$
where $R^1$, $R^2$, $R^3$, $R^5$, $R^6$, $R^8$, $R^9$, $R^{10}$, $R^{11}$, $R^{13}$, $R^{15}$, $R^{16}$ are each independently aliphatic, aromatic or fluoro containing monovalent hydrocarbon radicals containing from 1 to about 60 carbon atoms;

where $R^4$, $R^{12}$, $R^{17}$ are each monovalent radical bearing ion-pairs, where $R^7$, $R^{14}$ and $R^{18}$ are each independently selected from hydrogen, —$OR^{20}$, unsaturated monovalent radicals or monovalent epoxy group-containing radicals, monovalent sulfur atom-containing radicals and monovalent organosilane groups, wherein $R^{20}$ is independently selected from hydrogen, monovalent hydrocarbon radical of from 1 to about 60 carbon atoms, where the subscript a, b, c, d, e, f, g, h, i, j are zero or positive subject to the following limitations: the sum a+b+c+d+e+f+g+h+i+j is greater than or equal to 2 and less than or equal to 6000, b+e+h is greater than 0; and iii) an effective amount of precious metal catalyst suitable for facilitating addition cure reaction between i) and ii) to obtain a crosslinked ionic silicone network, (b) combining the crosslinked ionic silicone network of step (a), at least one cosmeceutical active, and optionally one or more cosmetically acceptable additives;

(c) shearing the combined components of step (b) during and/or after the combining step (b) with a solvent to form a crosslinked ionic silicone network gel, and (d) adding the crosslinked ionic silicone network gel to an oil phase to obtain the cosmetic composition.

2. The method of claim 1, wherein the crosslinked ionic silicone network gel comprises 0.1 to 99% of the crosslinked ionic silicone network obtain in step (a) and 0.01% to 25% of the cosmeceutical active.

3. The method of claim 1, wherein the monovalent radicals $R^4$, $R^{12}$, $R^{17}$ are each selected from the formula (II):

where A is a spacing group having selected from a divalent hydrocarbon and hydrocarbonoxy group, where superscripts n and y are independently from 1 to 6 and x is a product of n and y, where I is an ionic group independently selected from sulfonate —$SO_3^-$, sulfate —$OSO_3^-$, carboxylate —$COO^-$, phosphonate —$PO_3^{2-}$ and phosphate —$OPO_3^{2-}$ group, where M is hydrogen or a cation independently selected from alkali metals, alkaline earth metals, rare earth metals, transition metals, metals, metal complexes, quaternary ammonium, polymeric cations and phosphonium groups.

4. The method of claim 1 wherein the monovalent radicals $R^4$, $R^{12}$, $R^{17}$ are each independently selected from zwitterions having the formula (III):

where R' is a divalent hydrocarbon radical containing from 1 to about 60 carbon atoms, where R" is monovalent hydrocarbon radical containing from 1 to about 60 carbon atoms, and where R'" is divalent hydrocarbon radical containing from 2 to about 20 carbon atoms; and, I is an ionic group independently selected from sulfonate —$SO_3^-$, sulfate —$OSO_3^-$, carboxylate —$COO^-$, phosphonate —$PO_3^{2-}$ group and phosphate —$OPO_3^{2-}$ group.

5. The method of claim 1, wherein the crosslinking reaction mixture is reacted by condensation, hydrosilylation, free-radical polymerization, ring opening polymerization and combinations thereof.

6. The method of claim 5, wherein the reaction is carried out neat or in presence of the cosmetically acceptable additive.

7. The method of claim 1, wherein said crosslinked ionic silicone network comprises a physical blend of the ionic silicone of the formula (I) with structuring polymer and/or networks other than the said ionic silicone (I).

8. The method of claim 1 wherein the combined components of step (b) further comprises film-forming additives selected from the group comprising of polysilicone dimethicone, polysilicone acrylate copolymer, dimethylsiloxane/3-thiopropyl methyl siloxane copolymer, vinylpyyrolidone/vinylacetate copolymer, polyvinylacetate, starch, polyquaternium-4, polyquaternium-11, acrylates/steareth-2 methacrylate crosspolymer, vinylacetate/vinyl neodecanoate copolymer, polyester-5, cetyl ethylhexanoate, vinyl acetate, crotonate/vinyl neodecanoate copolymer, 2-acryamido-2-methyl propane sulfonic acid/acrylic acid copolymer, acryamido-2-methyl propane sulfonic acid/acrylic acid/acryl methacrylate copolymer, polyacrylamide, C13-C14 isoparaffin, laureth-7, octylacrylamide, acrylate/butylaminoethylmethacrylate copolymer, and combinations thereof.

9. The method of claim 1 wherein the combined components of step (b) further comprises cross-linked matrixes selected from the group comprising of non-ionic silicone cross-polymers, urethane cross-polymer, acrylated cross-polymers, cross-linked polysaccharides and combinations thereof.

10. The method of claim 1, wherein the cosmeceutical active is selected from the group consisting of photoprotective agents, self-tanning agents, desquamating agents, depigmenting agents, moisturizing agents, skin lightening agents, anti-aging ingredients, anti-wrinkle agents and combinations thereof.

11. The method of claim 1, wherein the crosslinked ionic silicone network obtain in step (a) is combined with the cosmetically acceptable additive prior to forming the combination with the cosmeceutical active.

12. The method of claim 1, wherein the cosmeceutical active is present in the crosslinking reaction mixture with the ionic silicone of formula (I).

13. The method of claim 1, wherein the cosmeceutical active is kept separate from the crosslinking reaction mixture with the ionic silicone of formula (I), and then both are combined following the formation of the ionic silicone network to form the crosslinked ionic silicone network gel in-situ during a topical application of the cosmetic composition.

14. A method of preparing a cosmetic composition comprising an oil phase and optionally an aqueous phase, wherein the method comprising 1) reacting a silicone hydride with an oxirane-functionalized ionic silicone, an oxirane ring-opening polymerization catalyst, a carrier solvent; and optionally, one or more silicon hydride activators to obtain a crosslinked ionic silicone network by the ring-opening polymerization of oxirane moiety with hydride;

2) shearing the crosslinked ionic silicone network of step 1) in the presence of at least one cosmeceutical active and optionally one or more cosmetically acceptable additives during and/or after polymerization of step 1) with at least a carrier solvent to form a crosslinked ionic silicone network gel; and 3) adding the crosslinked ionic silicone network gel of step 2) to an oil phase of the cosmetic composition;

wherein the oxirane-functionalized ionic silicone has the general formula (I):

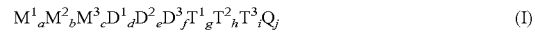

wherein:
$M^1 = R^1R^2R^3SiO_{1/2}$
$M^2 = R^4R^5R^6SiO_{1/2}$
$M^3 = R^7R^8R^9SiO_{1/2}$
$D^1 = R^{10}R^{11}SiO_{2/2}$
$D^2 = R^{12}R^{13}SiO_{2/2}$
$D^3 = R^{14}R^{15}SiO_{2/2}$
$T^1 = R^{16}SiO_{3/2}$
$T^2 = R^{17}SiO_{3/2}$
$T^3 = R^{18}SiO_{3/2}$
$Q = SiO_{4/2}$ where $R^1$, $R^2$, $R^3$, $R^5$, $R^6$, $R^8$, $R^9$, $R^{10}$, $R^{11}$, $R^{13}$, $R^{15}$, $R^{16}$ are each independently aliphatic, aromatic or fluoro containing monovalent hydrocarbon radicals containing from 1 to about 60 carbon atoms;

where $R^4$, $R^{12}$, $R^{17}$ are each monovalent radical bearing ion-pairs, where $R^7$, $R^{14}$ and $R^{18}$ are each independently selected from hydrogen, $-OR^{20}$, unsaturated monovalent radicals or monovalent epoxy group-containing radicals, monovalent sulfur atom-containing radicals and monovalent organosilane groups, wherein $R^{20}$ is independently selected from hydrogen, monovalent hydrocarbon radical of from 1 to about 60 carbon atoms, where the subscript a, b, c, d, e, f, g, h, i, j are zero or positive subject to the following limitations: the sum a+b+c+d+e+f+g+h+i+j is greater than or equal to 2 and less than or equal to 6000, b+e+h is greater than 0.

15. The method of claim 14 wherein the monovalent radicals $R^4$, $R^{12}$, $R^{17}$ are selected from the formula (II):

$$-A\text{-}I^{x-}M_n^{y+}; \qquad (II)$$

where A is a spacing group having selected from a divalent hydrocarbon and hydrocarbonoxy group, where superscripts n and y are independently from 1 to 6 and x is a product of n and y, where I is an ionic group independently selected from sulfonate $-SO_3^-$, sulfate $-OSO_3^-$, carboxylate $-COO^-$, phosphonate $-PO_3^{2-}$ and phosphate $-OPO_3^{2-}$ group, more specifically sulfonate $-SO_3^-$, where M is hydrogen or a cation independently selected from alkali metals, alkaline earth metals, rare earth metals, transition metals, metals, metal complexes, quaternary ammonium, polymeric cations and phosphonium groups.

16. The method of claim 14 wherein the monovalent radicals $R^4$, $R^{12}$, $R^{17}$ are independently selected from zwitterions having the formula (III):

$$-R'-NR''_2{}^+-R'''-I \qquad (III)$$

where R' is a divalent hydrocarbon radical containing from 1 to about 60 carbon atoms, where R" is monovalent hydrocarbon radical containing from 1 to about 60 carbon atoms, and where R'" is divalent hydrocarbon radical containing from 2 to about 20 carbon atoms; and, I is an ionic group independently selected from sulfonate $-SO_3^-$, sulfate $-OSO_3^-$, carboxylate $-COO^-$, phosphonate $-PO_3^{2-}$ group and phosphate $-OPO_3^{2-}$ group.

17. The method claim 14 wherein the crosslinking reaction mixture is reacted by condensation, hydrosilylation, free-radical polymerization, ring opening polymerization and combinations thereof.

18. The method of claim 14 wherein the cosmeceutical active is selected from the group consisting of photoprotective agents, self-tanning agents, desquamating agents, depigmenting agents, moisturizing agents, skin lightening agents, anti-aging ingredients, anti-wrinkle agents and combinations thereof.

* * * * *